United States Patent
Kochba et al.

(10) Patent No.: US 10,506,943 B2
(45) Date of Patent: Dec. 17, 2019

(54) METHODS AND SYSTEMS FOR MONITORING INTRABODY TISSUES

(71) Applicant: Sensible Medical Innovations Ltd., Kfar Neter (IL)

(72) Inventors: Ilan Kochba, Modiln (IL); Dan Rappaport, Tel-Aviv (IL); Amir Saroka, Tel-Aviv (IL); Shlomi Bergida, Udim (IL); Nadav Mizrahi, Tel-Aviv (IL); Amir Ronen, Ramot Menashe (IL)

(73) Assignee: Sensible Medical Innovations Ltd., Netanya (IL)

( * ) Notice: Subject to any disclaimer, the term of this patent is extended or adjusted under 35 U.S.C. 154(b) by 0 days.

(21) Appl. No.: 15/436,902

(22) Filed: Feb. 20, 2017

(65) Prior Publication Data

US 2017/0156626 A1    Jun. 8, 2017

Related U.S. Application Data

(63) Continuation of application No. 13/254,852, filed as application No. PCT/IL2010/000182 on Mar. 4, (Continued)

(51) Int. Cl.
*A61B 5/05* (2006.01)
*A61B 5/00* (2006.01)
(Continued)

(52) U.S. Cl.
CPC .............. *A61B 5/05* (2013.01); *A61B 5/0075* (2013.01); *A61B 5/0507* (2013.01);
(Continued)

(58) Field of Classification Search
None
See application file for complete search history.

(56) References Cited

U.S. PATENT DOCUMENTS

| 3,534,727 A | 10/1970 | Roman |
| 4,016,868 A | 4/1977 | Allison |
| (Continued) | | |

FOREIGN PATENT DOCUMENTS

| CA | 2898342 | 7/2014 |
| EP | 0694282 | 1/1996 |
| (Continued) | | |

OTHER PUBLICATIONS

A Microwave Method for Measuring Changes in Lung Water Content: Numerical Simulation by Iskander et al. IEEE Transactions on Biomedical Engineering, vol. BME-28, No. 12, Dec. 1981.*

(Continued)

*Primary Examiner* — Katherine L Fernandez
*Assistant Examiner* — Michael S Kellogg

(57) ABSTRACT

A method for monitoring an intrabody region of a patient. The method comprises intercepting electromagnetic (EM) radiation from the intrabody region in a plurality of EM radiation sessions during a period of at least 6 hours, calculating a dielectric related change of the intrabody region by analyzing respective the intercepted EM radiation, detecting a physiological pattern according to said dielectric related change and outputting a notification indicating the physiological pattern.

14 Claims, 7 Drawing Sheets

Related U.S. Application Data 2010, now Pat. No. 9,572,511, said application No. 13/254,852 is a continuation-in-part of application No. 12/676,381, filed as application No. PCT/IL2008/001199 on Sep. 4, 2008, said application No. 13/254,852 is a continuation-in-part of application No. 12/676,385, filed as application No. PCT/IL2008/001198 on Sep. 4, 2008, now abandoned.

(60) Provisional application No. 61/157,261, filed on Mar. 4, 2009, provisional application No. 60/969,966, filed on Sep. 5, 2007, provisional application No. 60/969,963, filed on Sep. 5, 2007, provisional application No. 60/969,965, filed on Sep. 5, 2007.

(51) Int. Cl.
*A61B 5/021* (2006.01)
*A61B 5/024* (2006.01)

(52) U.S. Cl.
CPC ............ *A61B 5/4076* (2013.01); *A61B 5/412* (2013.01); *A61B 5/4504* (2013.01); *A61B 5/4842* (2013.01); *A61B 5/4848* (2013.01); *A61B 5/7246* (2013.01); *A61B 5/7282* (2013.01); *A61B 5/0059* (2013.01); *A61B 5/021* (2013.01); *A61B 5/024* (2013.01); *A61B 5/4869* (2013.01); *A61B 5/72* (2013.01)

(56) References Cited

U.S. PATENT DOCUMENTS

| | | |
|---|---|---|
| 4,240,445 A * | 12/1980 | Iskander ............ A61B 5/05 219/780 |
| 4,279,257 A | 7/1981 | Hochstein |
| 4,381,510 A | 4/1983 | Wren |
| 4,488,559 A * | 12/1984 | Iskander ............ A61B 5/05 600/430 |
| 4,572,197 A | 2/1986 | Moore et al. |
| 4,580,572 A | 4/1986 | Granek et al. |
| 4,647,281 A | 3/1987 | Carr |
| 4,676,252 A | 6/1987 | Trautman et al. |
| 4,690,149 A | 9/1987 | Ko |
| 4,877,034 A | 10/1989 | Atkins et al. |
| 4,920,969 A | 5/1990 | Suzuki et al. |
| 4,926,868 A | 5/1990 | Larsen |
| 4,958,638 A * | 9/1990 | Sharpe ............ A61B 5/02 128/653 |
| 4,991,585 A | 2/1991 | Mawhinney |
| 5,002,060 A | 3/1991 | Nedivi |
| 5,078,134 A | 1/1992 | Heilman et al. |
| 5,132,623 A | 7/1992 | De et al. |
| 5,282,840 A | 2/1994 | Hudrlik |
| 5,334,141 A | 8/1994 | Carr et al. |
| 5,363,050 A | 11/1994 | Guo et al. |
| 5,394,882 A | 3/1995 | Mawhinney |
| 5,479,120 A | 12/1995 | McEwan |
| 5,517,198 A | 5/1996 | McEwan |
| 5,523,760 A | 6/1996 | McEwan |
| 5,563,605 A | 10/1996 | McEwan |
| 5,573,012 A | 11/1996 | McEwan |
| 5,576,627 A | 11/1996 | McEwan |
| 5,604,531 A | 2/1997 | Iddan et al. |
| 5,728,143 A | 3/1998 | Gough et al. |
| 5,738,102 A | 4/1998 | Lemelson |
| 5,749,369 A | 5/1998 | Rabinovich et al. |
| 5,766,208 A | 6/1998 | McEwan |
| 5,804,921 A | 9/1998 | McEwan et al. |
| 5,805,110 A | 9/1998 | McEwan |
| 5,807,257 A | 9/1998 | Bridges |
| 5,829,437 A | 11/1998 | Bridges |
| 5,833,711 A | 11/1998 | Schneider, Sr. |
| 5,861,019 A | 1/1999 | Sun et al. |
| 5,876,353 A | 3/1999 | Riff |
| 5,883,591 A | 3/1999 | McEwan |
| 5,947,910 A | 9/1999 | Zimmet |
| 5,957,861 A | 9/1999 | Combs et al. |
| 5,964,703 A | 10/1999 | Goodman et al. |
| 5,995,863 A | 11/1999 | Farace et al. |
| 6,015,386 A | 1/2000 | Kensey et al. |
| 6,026,173 A | 2/2000 | Svenson et al. |
| 6,061,589 A | 5/2000 | Bridges et al. |
| 6,064,903 A | 5/2000 | Riechers et al. |
| 6,111,415 A | 8/2000 | Moshe |
| 6,169,925 B1 | 1/2001 | Villaseca et al. |
| 6,211,663 B1 | 4/2001 | Moulthrop et al. |
| 6,233,479 B1 | 5/2001 | Haddad et al. |
| 6,236,889 B1 | 5/2001 | Soykan et al. |
| 6,281,843 B1 | 8/2001 | Evtioushkine et al. |
| 6,330,479 B1 | 12/2001 | Stauffer |
| 6,332,087 B1 | 12/2001 | Svenson et al. |
| 6,332,091 B1 | 12/2001 | Burns et al. |
| 6,351,246 B1 | 2/2002 | McCorkle |
| 6,417,797 B1 | 7/2002 | Cousins et al. |
| 6,425,878 B1 | 7/2002 | Shekalim |
| 6,459,931 B1 | 10/2002 | Hirschman |
| 6,484,047 B1 | 11/2002 | Vilsmeier |
| 6,487,428 B1 | 11/2002 | Culver et al. |
| 6,488,677 B1 | 12/2002 | Bowman et al. |
| 6,494,829 B1 | 12/2002 | New, Jr. et al. |
| 6,496,711 B1 | 12/2002 | Athan et al. |
| 6,512,949 B1 | 1/2003 | Combs et al. |
| 6,551,252 B2 | 4/2003 | Sackner et al. |
| 6,574,510 B2 | 6/2003 | Von Arx et al. |
| 6,577,709 B2 | 6/2003 | Tarr |
| 6,590,545 B2 | 7/2003 | McCorkle |
| 6,675,045 B2 | 1/2004 | Mass et al. |
| 6,682,480 B1 | 1/2004 | Habib et al. |
| 6,687,523 B1 | 2/2004 | Jayaramen et al. |
| 6,746,404 B2 | 6/2004 | Schwartz |
| 6,766,201 B2 | 7/2004 | Von Arx et al. |
| 6,770,070 B1 | 8/2004 | Balbierz |
| 6,783,499 B2 | 8/2004 | Schwartz |
| 6,788,262 B1 | 9/2004 | Adams et al. |
| 6,802,811 B1 | 10/2004 | Slepian |
| 6,809,701 B2 | 10/2004 | Amundson et al. |
| 6,849,046 B1 | 2/2005 | Eyal-Bickels et al. |
| 6,909,397 B1 | 6/2005 | Greneker, III et al. |
| 6,917,833 B2 | 7/2005 | Denker et al. |
| 6,954,673 B2 | 10/2005 | Von Arx et al. |
| 6,972,725 B1 | 12/2005 | Adams |
| 7,006,856 B2 | 2/2006 | Baker, Jr. et al. |
| 7,024,248 B2 | 4/2006 | Penner et al. |
| 7,047,058 B1 | 5/2006 | Dvorsky et al. |
| 7,072,718 B2 | 7/2006 | Von Arx et al. |
| 7,077,810 B2 | 7/2006 | Lange et al. |
| 7,110,823 B2 | 9/2006 | Whitehurst et al. |
| 7,116,276 B2 | 10/2006 | Lee |
| 7,122,012 B2 | 10/2006 | Bouton et al. |
| 7,135,871 B1 | 11/2006 | Pelletier |
| 7,229,415 B2 | 6/2007 | Schwartz |
| 7,228,047 B1 | 7/2007 | Szilagyi et al. |
| 7,315,170 B2 | 1/2008 | Sakayori |
| 7,316,658 B2 | 1/2008 | Gagne |
| 7,330,034 B1 | 2/2008 | Pelletier et al. |
| 7,387,610 B2 | 6/2008 | Stahmann et al. |
| 7,445,605 B2 | 11/2008 | Overall et al. |
| 7,450,077 B2 | 11/2008 | Waterhouse et al. |
| 7,483,752 B2 | 1/2009 | Von Arx et al. |
| 7,561,908 B2 | 7/2009 | Glukhovsky et al. |
| 7,591,792 B2 | 9/2009 | Bouton |
| 7,613,522 B2 | 11/2009 | Christman et al. |
| 7,628,757 B1 | 12/2009 | Koh |
| 7,674,244 B2 | 3/2010 | Kalafut et al. |
| 7,686,762 B1 | 3/2010 | Najafi et al. |
| 7,725,150 B2 | 5/2010 | Tupin, Jr. et al. |
| 7,729,776 B2 | 6/2010 | Von Arx et al. |
| 7,736,309 B2 | 6/2010 | Miller et al. |
| 7,756,587 B2 | 7/2010 | Penner et al. |
| 7,825,667 B2 | 11/2010 | Fang et al. |
| 7,837,629 B2 | 11/2010 | Bardy |
| 7,844,341 B2 | 11/2010 | Von Arx et al. |
| 7,860,574 B2 | 12/2010 | Von Arx et al. |

(56) References Cited

U.S. PATENT DOCUMENTS

| | | | |
|---|---|---|---|
| 7,872,613 | B2 | 1/2011 | Keilman et al. |
| 8,032,199 | B2 | 10/2011 | Linti et al. |
| 8,235,949 | B2 | 8/2012 | Hack et al. |
| 2003/0036674 | A1 | 2/2003 | Bouton |
| 2003/0036713 | A1* | 2/2003 | Bouton .................. A61B 5/05 600/587 |
| 2003/0128808 | A1 | 7/2003 | Kindlein et al. |
| 2004/0006279 | A1 | 1/2004 | Arad (Abboud) |
| 2004/0073093 | A1 | 4/2004 | Hatlestad |
| 2004/0148021 | A1 | 7/2004 | Cartledge et al. |
| 2004/0186395 | A1 | 9/2004 | Vastano |
| 2004/0249257 | A1 | 12/2004 | Tupin, Jr. et al. |
| 2004/0249258 | A1 | 12/2004 | Tupin, Jr. et al. |
| 2004/0254457 | A1 | 12/2004 | Van der Weide |
| 2005/0065567 | A1 | 3/2005 | Lee et al. |
| 2005/0107719 | A1* | 5/2005 | Arad (Abboud) ..... A61B 5/05 600/547 |
| 2005/0124908 | A1 | 6/2005 | Belalcazar et al. |
| 2005/0149139 | A1 | 7/2005 | Plicchi et al. |
| 2005/0171396 | A1 | 8/2005 | Pankratov et al. |
| 2005/0177061 | A1 | 8/2005 | Alanen et al. |
| 2006/0058606 | A1 | 3/2006 | Davis et al. |
| 2006/0235289 | A1 | 10/2006 | Wesselink et al. |
| 2006/0258952 | A1 | 11/2006 | Stahmann et al. |
| 2006/0293609 | A1 | 12/2006 | Stahmann et al. |
| 2007/0032749 | A1 | 2/2007 | Overall et al. |
| 2007/0066904 | A1 | 3/2007 | Wiesmann et al. |
| 2007/0088221 | A1 | 4/2007 | Stahmann |
| 2007/0123770 | A1 | 5/2007 | Bouton et al. |
| 2007/0163584 | A1 | 7/2007 | Bohm et al. |
| 2007/0197878 | A1* | 8/2007 | Shklarski ........... A61B 5/02055 600/300 |
| 2007/0238914 | A1 | 10/2007 | Royality et al. |
| 2008/0097530 | A1 | 4/2008 | Muccio et al. |
| 2008/0103440 | A1 | 5/2008 | Ferren et al. |
| 2008/0200802 | A1 | 8/2008 | Bhavaraju et al. |
| 2008/0200803 | A1 | 8/2008 | Kwon et al. |
| 2008/0224688 | A1 | 9/2008 | Rubinsky et al. |
| 2008/0269589 | A1 | 10/2008 | Thijs et al. |
| 2008/0283290 | A1 | 11/2008 | Niino et al. |
| 2008/0288028 | A1 | 11/2008 | Larson et al. |
| 2009/0043223 | A1 | 2/2009 | Zhang et al. |
| 2009/0149918 | A1 | 6/2009 | Krulevitch et al. |
| 2009/0227882 | A1 | 9/2009 | Foo |
| 2009/0228001 | A1 | 9/2009 | Pacey |
| 2009/0228075 | A1 | 9/2009 | Dion |
| 2009/0241972 | A1 | 10/2009 | Keilman et al. |
| 2009/0248129 | A1 | 10/2009 | Keilman et al. |
| 2010/0056907 | A1 | 3/2010 | Rappaport et al. |
| 2010/0256462 | A1 | 10/2010 | Rappaport et al. |
| 2011/0025295 | A1 | 2/2011 | Saroka et al. |
| 2011/0319746 | A1 | 12/2011 | Kochba et al. |
| 2013/0281800 | A1 | 10/2013 | Saroka et al. |

FOREIGN PATENT DOCUMENTS

| | | |
|---|---|---|
| EP | 1600892 | 11/2005 |
| JP | 2004-528864 | 9/2004 |
| JP | 2005-531386 | 10/2005 |
| JP | 2005-334298 | 12/2005 |
| JP | 2007-509353 | 4/2007 |
| WO | WO 99/39728 | 8/1999 |
| WO | WO 00/71207 | 11/2000 |
| WO | WO 02/053228 | 7/2002 |
| WO | WO 03/009753 | 2/2003 |
| WO | WO 2004/004539 | 1/2004 |
| WO | WO 2005/043100 | 5/2005 |
| WO | WO 2005/074361 | 8/2005 |
| WO | WO 2005/094369 | 10/2005 |
| WO | WO 2007/010460 | 1/2007 |
| WO | WO 2007/055491 | 5/2007 |
| WO | WO 2008/002251 | 1/2008 |
| WO | WO 2008/122056 | 10/2008 |
| WO | WO 2009/031149 | 3/2009 |
| WO | WO 2009/031150 | 3/2009 |
| WO | WO 2011/141915 | 11/2011 |

OTHER PUBLICATIONS

Stress Testing in Valve Disease by Pierard et al. Heart 2007;93:766-772. doi: 10.1136/hrt.2005.074815.*
Electronic packaging by Wikipedia, pub. online on Dec. 2006 at <https://en.wikipedia.org/w/index.php?title=Electronic_packaging&oldid=927795761>.*
Advisory Action Before the Filing of an Appeal Brief dated Mar. 2, 2016 From the US Patent and Trademark Office Re. U.S. Appl. No. 12/676,381.
Advisory Action Before the Filing of an Appeal Brief dated Jun. 6, 2013 From the US Patent and Trademark Office Re. U.S. Appl. No. 12/676,385.
Advisory Action Before the Filing of an Appeal Brief dated Mar. 18, 2015 From the US Patent and Trademark Office Re. U.S. Appl. No. 12/544,314.
Advisory Action Before the Filing of an Appeal Brief dated Oct. 21, 2015 From the US Patent and Trademark Office Re. U.S. Appl. No. 13/254,852.
Advisory Action Before the Filing of an Appeal Brief dated Apr. 22, 2014 From the US Patent and Trademark Office Re. U.S. Appl. No. 13/254,852.
Applicant-Initiated Interview Summary dated Jul. 2, 2013 From the US Patent and Trademark Office Re. U.S. Appl. No. 12/676,381.
Applicant-Initiated Interview Summary dated Dec. 11, 2013 From the US Patent and Trademark Office Re. U.S. Appl. No. 12/544,314.
Applicant-Initiated Interview Summary dated Jun. 13, 2013 From the US Patent and Trademark Office Re. U.S. Appl. No. 12/676,385.
Applicant-Initiated Interview Summary dated May 16, 2014 From the US Patent and Trademark Office Re. U.S. Appl. No. 13/254,852.
Applicant-Initiated Interview Summary dated Feb. 20, 2015 From the US Patent and Trademark Office Re. U.S. Appl. No. 13/254,852.
Communciation Pursuant to Article 94(3) EPC dated Aug. 4, 2014 From the European Patent Office Re. Application No. 08808013.0.
Communciation Pursuant to Article 94(3) EPC dated Sep. 27, 2013 From the European Patent Office Re. Application No. 08808013.0.
Communication Pursuant to Article 94(3) EPC dated May 6, 2013 From the European Patent Office Re. Application No. 10712583.3.
Communication Pursuant to Article 94(3) EPC dated Apr. 16, 2015 From the European Patent Office Re. Application No. 10712583.3.
Communication Pursuant to Article 94(3) EPC dated Feb. 19, 2016 From the European Patent Office Re. Application No. 08789867.2.
Communication Pursuant to Article 94(3) EPC dated Mar. 19, 2014 From the European Patent Office Re. Application No. 08789867.2.
Communication Pursuant to Article 94(3) EPC Dated May 22, 2014 From the European Patent Office Re. Application No. 10712583.3.
Communication Pursuant to Article 94(3) EPC dated Apr. 29, 2015 From the European Patent Office Re. Application No. 08789867.2.
Communication Pursuant to Article 94(3) EPC dated Oct. 29, 2013 From the European Patent Office Re. Application No. 08789867.2.
Examiner-Initiated Interview Summary dated Feb. 4, 2016 From the US Patent and Trademark Office Re. U.S. Appl. No. 12/676,381.
International Preliminary Report on Patentability dated Sep. 15, 2011 From the International Bureau of WIPO Re. Application No. PCT/IL2010/000182.
International Preliminary Report on Patentability dated Mar. 18, 2010 From the International Bureau of WIPO Re. Application No. PCT/IL2008/001198.
International Preliminary Report on Patentability dated Mar. 18, 2010 From the International Bureau of WIPO Re. Application No. PCT/IL2008/001199.
International Search Report and the Written Opinion dated Jun. 15, 2010 From the International Searching Authority Re. Application No. PCT/IL2010/000182.
International Search Report dated Feb. 4, 2009 From the International Searching Authority Re. Application No. PCT/IL2008/001198.

(56) References Cited

OTHER PUBLICATIONS

International Search Report dated Jan. 23, 2009 From the International Searching Authority Re. Application No. PCT/IL2008/001199.
Notice of Reason for Rejection dated Oct. 23, 2015 From the Japanese Patent Office Re. Application No. 2015-000023 and Its Translation Into English.
Notice of Reason for Rejection dated Jan. 31, 2014 From the Japanese Patent Office Re. Application No. 2010-523644 and Its Translation Into English.
Office Action dated Jun. 5, 2013 From the Israel Patent Office Re. Application No. 214973 and Its Translation Into English.
Office Action dated Dec. 14, 2015 From the Israel Patent Office Re. Application No. 239240 and Its Translation Into English.
Office Action dated Apr. 28, 2014 From the Israel Patent Office Re. Application No. 214973 and Its Translation Into English.
Official Action dated Jul. 1, 2014 From the US Patent and Trademark Office Re. U.S. Appl. No. 12/676,381.
Official Action dated Oct. 2, 2015 From the US Patent and Trademark Office Re. U.S. Appl. No. 13/922,299.
Official Action dated Nov. 3, 2014 From the US Patent and Trademark Office Re. U.S. Appl. No. 12/544,314.
Official Action dated Apr. 4, 2012 From the US Patent and Trademark Office Re. U.S. Appl. No. 12/676,385.
Official Action dated Sep. 4, 2014 From the US Patent and Trademark Office Re. U.S. Appl. No. 13/254,852.
Official Action dated Jul. 5, 2013 From the US Patent and Trademark Office Re. U.S. Appl. No. 12/846,861.
Official Action dated May 7, 2015 From the US Patent and Trademark Office Re. U.S. Appl. No. 12/676,381.
Official Action dated Oct. 7, 2015 From the US Patent and Trademark Office Re. U.S. Appl. No. 12/676,381.
Official Action dated Feb. 8, 2013 From the US Patent and Trademark Office Re. U.S. Appl. No. 12/676,381.
Official Action dated Mar. 9, 2017 From the US Patent and Trademark Office Re. U.S. Appl. No. 13/922,299. (40 pages).
Official Action dated Jun. 10, 2015 From the US Patent and Trademark Office Re. U.S. Appl. No. 13/254,852.
Official Action dated Apr. 11, 2016 From the US Patent and Trademark Office Re. U.S. Appl. No. 12/676,381.
Official Action dated Mar. 11, 2014 From the US Patent and Trademark Office Re. U.S. Appl. No. 12/544,314.
Official Action dated Oct. 11, 2013 From the US Patent and Trademark Office Re. U.S. Appl. No. 12/544,314.
Official Action dated Dec. 12, 2013 From the US Patent and Trademark Office Re. U.S. Appl. No. 13/254,852.
Official Action dated Jul. 13, 2016 From the US Patent and Trademark Office Re. U.S. Appl. No. 12/544,314.
Official Action dated Sep. 13, 2012 From the US Patent and Trademark Office Re. U.S. Appl. No. 12/676,381.
Official Action dated Mar. 14, 2016 From the US Patent and Trademark Office Re. U.S. Appl. No. 13/254,852.
Official Action dated Oct. 15, 2012 From the US Patent and Trademark Office Re. U.S. Appl. No. 12/846,861.
Official Action dated Dec. 19, 2012 From the US Patent and Trademark Office Re. U.S. Appl. No. 12/544,314.
Official Action dated Dec. 20, 2012 From the US Patent and Trademark Office Re. U.S. Appl. No. 12/676,385.
Official Action dated Oct. 22, 2013 From the US Patent and Trademark Office Re. U.S. Appl. No. 12/676,381.
Official Action dated Mar. 25, 2013 From the US Patent and Trademark Office Re. U.S. Appl. No. 13/254,852.
Official Action dated May 25, 2016 From the US Patent and Trademark Office Re. U.S. Appl. No. 13/922,299.
Official Action dated Sep. 25, 2015 From the US Patent and Trademark Office Re. U.S. Appl. No. 12/544,314.
Official Action dated Feb. 26, 2014 From the US Patent and Trademark Office Re. U.S. Appl. No. 12/846,861.
Official Action dated Dec. 27, 2016 From the US Patent and Trademark Office Re. U.S. Appl. No. 12/676,381. (37 pages).
Restriction Official Action dated Jul. 2, 2015 From the US Patent and Trademark Office Re. U.S. Appl. No. 13/922,299.
Restriction Official Action dated Jun. 7, 2012 From the US Patent and Trademark Office Re. U.S. Appl. No. 12/544,314.
Summons to Attend Oral Proceedings Pursuant to Rule 115(1) EPC dated Mar. 16, 2016 From the European Patent Office Re. Application No. 10712583.3.
Summons to Attend Oral Proceedings Pursuant to Rule 115(1) EPC dated Dec. 23, 2016 From the European Patent Office Re. Application No. 08789867.2. (4 Pages).
Supplementary European Search Report and the European Search Opinion dated Feb. 13, 2013 From the European Patent Office Re. Application No. 08789867.2.
Supplementary European Search Report and the European Search Opinion dated Feb. 14, 2013 From the European Patent Office Re. Application No. 08808013.0.
Translation of Notice of Reason for Rejection dated Sep. 24, 2013 From the Japanese Patent Office Re. Application No. 2010-523644.
Translation of Reason for Rejection dated Jul. 29, 2016 From the Japanese Patent Office Re. Application No. 2015-000023.
Written Opinion dated Feb. 4, 2009 From the International Searching Authority Re. Application No. PCT/IL2008/001198.
Written Opinion dated Jan. 23, 2009 From the International Searching Authority Re. Application No. PCT/IL2008/001199.
Azevedo et al "Micropower Impulse Radar", Science & Technologies Review, 17-29, Feb. 1996.
Billich "Bio-Medical Sensing Using Ultra Wideband Communications and Radar Technology", PhD Proposal, Department of Information and Telecommunication Technology—University of Trento, Italy—Jan. 2006 (10 pages).
Fear et al. "Enhancing Breast Tumor Detection With Near-Field Imaging", IEEE Microwave Magazine, pp. 48-56, Mar. 2002.
Fear et al. "Microwaves for Breast Cancer Detection", IEEE Potentials, 22(1): 12-18, Feb. 25, 2003.
Gabriel "Compilation of the Dielectric Properties of Body Tissues at RF and Microwave Frequencies", Final Technical Report for the Period Sep. 15, 1993 to Dec. 14, 1994, p. 1-21, Jan. 1996.
Gentili et al "A Versatile Microwave Plethysmograph for the Monitoring of Physiological Parameters", IEEE Transactions on Biomedical Engineering 49(10) 1204-1210, Oct. 2002.
Hill-Rom "The Vest® Airway Clearance System. Information for Physicians", Hill-Rom, Retrieved From the Internet, 3 P., Nov. 24, 2011.
Jafari et al. "Ultrawideband Radar Imagingn System for Biomedical Applications", Journal of Vacuum Science and Technology A: Vacuum, Surfaces, and Films, 24(3): 752-757, May/Jun. 2006.
Jiang et al. "Ultrasound-Guided Microwave Imaging of Breast Cancer: Tissue Phantom and Pilot Clinical Experiments", Medical Physics, 32(8): 2528-2535, Aug. 2005.
Juweid et al. "Positron-Emission Tomography and Assessment of Cancer Therapy", The New England Journal of Medicine, 354(5): 496-507, Feb. 2, 2006.
Kagawa et al. "Advanced Exercise Control Using Miniature ECG and 3D Acceleration Sensors", D&D Forum on Telemedicine Systems: Issues, design, Development and Standardization at Globecom 2008, New Orleans, Louisiana, USA, 23 P., Dec. 2, 2008.
Katzeff et al. "Exercise Stress Testing and an Electromechanical S Wace of the Electrocardiogram", South African Medical Journal, 49(27): 1088-1090, Jun. 28, 1975.
Kerckhoffs et al. "Homogeneity of Cardiac Contraction Despite Physiological Asynchrony of Depolarization: A Model Study", Annals of Biomedical Engineering, 31: 536-547, 2003.
Kramer et al. "Dielectric Measurement of Cerebral Water Content Using a Network Analyzer", Neurological Research, 14: 255-258, Jun. 1992.
Lee et al. "Noninvasive Tests in Patients With Stable Coronary Artery Disease", The New England Journal of Medicine, 344(24): 1840-1845, Jun. 14, 2001.
Li et al. "An Overview of Ultra-Wideband Microwave Imaging via Space-Time Beamforming for Early-Stage Breast-Cancer Detection", IEEE Antennas and Propagation Magazine, 47(1): 19-34, Feb. 2005.

(56) References Cited

OTHER PUBLICATIONS

Meaney et al. "Microwave Imaging for Neoadjuvant Chemotherapy Monitoring", First European Conference on Antennas and Propagation, EuCAP 2006, Nice, France, Nov. 6-10, 2006, p. 1-4, Nov. 2006.
Meaney et al. "Near-Field Microwave Imaging of Biologically-Based Materials Using a Monopole Transceiver System", IEEE Transactions on Microwave Theory and Techniques, 46(1): 31-45, Jan. 1998.
Nopp et al. "Dielectric Properties of Lung Tissue as a Function of Air Content", Physics in Medicine and Biology, 38(6): 699-716, Jun. 1993.
Panetta "A Mathematical Model of Periodically Pulsed Chemotherapy: Tumor Recurrence and Metastasis in a Competitive Environment", Bulletin of Methematical Biology, 58(3): 425-447, 1996.
Park et al. "An Ultra-Wearable, Wireless, Low Power ECG Monitoring System", Proceedings of the IEEE Biomedical Circuits and Systems Conference, BioCAS 2006, London, UK, p. 241-244, Nov. 29-Dec. 1, 2006.
Pedersen et al "An Investigation of the Use of Microwave Radiation for Pulmonary Diagnostics", IEEE Transactions on Biomedical Engineering, 23(5): 410-412, Sep. 1976.
Schantz "Introduction to Ultra-Wideband Antennas", IEEE Conference, On Ultra Wideband Systems and Technologies, in Brownsboro, AL, USA, on Nov. 16-19, 2003, p. 1-9, 2003.
Schiller "Noninvasive Monitoring of Tumors", The New England Journal of Medicine, 359(4): 418-420, Jul. 24, 2008.
Semenov et al. "Three-Dimensional Microwave Tomography: Initial Experimental Imaging of Animals", IEEE Transactions on Biomedical Engineering, XP011007196, 49(1): 55-63, Jan. 2002. Abstract, p. 56, col. 1, Lines 6, 7.
Shea et al. "Contrast-Enhanced Microwave Imaging of Breast Tumors: A Computational Study Using 3D Realistic Numerical Phantoms", Inverse Problems, 26: 1-22, 2010.
Smiseth et al. "Regional Left Ventricular Electric and Mechanical Activation and Relaxation", JACC, Journal of the American College of Cardiology, 47(1): 173-174, Jan. 3, 2006.
Thornton "Optimization of Protocols for Computed Tomography Coronary Angiography", Supplement to Applied Radiology, p. 54-62, Jun. 2002.
Winters et al. "Estimation of the Frequency-Dependent Average Dielectric Properties of Breast Tissue Using a Time-Domain Inverse Scattering Technique" IEEE Transactions on Antennas and Propagation, 54(11): 3517-3528, Nov. 2006.
Winters et al. "Three-Dimensional Microwave Breast Imaging: Dispersive Dielectric Properties Estimation Using Patient-Specific Basis Functions", IEEE Transactions on Medical Imaging, 28(7): 969-981, Jul. 2007.
Yamokoski et al "OptiVol® Fluid Status Monitoring With an Implantable Cardiac Device: A Heart Failure Managaement System.", 4:(6) 775-780 (doi:10.1586/17434440.4.6.775), Nov. 2007.
Zhou et al. "On the Resolution of UWB Microwave Imaging of Tumors in Random Breast Tissue", IEEE International Symposium of the Antennas and Propagation Society, Jul. 3-8, 2005, 3A: 831-834, Jul. 2005.
Zito et al "Wearable System-On-A-Chip Pulse Radar Sensors for the Health Care: System Overview", 21st Conference on Advanced Information Networking and Applications Workshop (AINAW'07), University of Pisa, Italy—2007, IEEE.
Zlochiver et al "A Portable Bio-Impedance System for Monitoring Lung Resistivity", Medical Engineering & Physics, 29(1): 93-100, 2007.
Official Action dated May 25, 2017 From the US Patent and Trademark Office Re. U.S. Appl. No. 12/544,314. (33 pages).
Interview Summary dated Jun. 8, 2017 From the US Patent and Trademark Office Re. U.S. Appl. No. 13/922,299. (3 pages).
Official Action dated Aug. 10, 2017 From the US Patent and Trademark Office Re. U.S. Appl. No. 13/922,299. (26 pages).
European Search Report and the European Search Opinion dated Apr. 3, 2017 From the European Patent Office Re. Application No. 17153865.5. (7 Pages).
Official Action dated Apr. 4, 2018 From the US Patent and Trademark Office Re. U.S. Appl. No. 12/544,314. (22 pages).
Official Action dated Aug. 2, 2018 From the US Patent and Trademark Office Re. U.S. Appl. No. 12/676,381. (19 pages).
European Search Report and the European Search Opinion dated Sep. 20, 2018 From the European Patent Office Re. Application No. 17020594.2. (7 pages).
Applicant-Initiated Interview Summary dated Feb. 5, 2019 From the US Patent and Trademark Office Re. U.S. Appl. No. 12/676,381. (4 pages).
Communication Pursuant to Article 94(3) EPC dated Dec. 17, 2018 From the European Patent Office Re. Application No. 17153865.5. (6 Pages).
Official Action dated Jan. 3, 2019 From the US Patent and Trademark Office Re. U.S. Appl. No. 12/676,381. (14 pages).
Semenov et al. "Dielectrical Spectroscopy of Canine Myocardium During Acute Ischemia and Hypoxia at Frequency Spectrum From 100 kHz to 6 GHz", IEEE Transactions on Medical Imaging, XP011076314, 21(6): 703-707, Jun. 2002.
Communication Pursuant to Article 94(3) EPC dated May 18, 2018 From the European Patent Office Re. Application No. 17153865.5. (4 Pages).
Official Action dated Dec. 28, 2017 From the US Patent and Trademark Office Re. U.S. Appl. No. 12/676,381. (23 pages).
Official Action dated Jun. 29, 2018 From the US Patent and Trademark Office Re. U.S. Appl. No. 13/922,299. (27 pages).
McClelland et al. "A Continuous 40 Motion Model from Multiple Respiratory Cycles for Use in Lung Radiotherapy", Medical Physics, 33(9): 3348-3358, Sep. 2006.
Official Action dated Mar. 15, 2019 From the US Patent and Trademark Office Re. U.S. Appl. No. 12/544,314. (5 Pages).

* cited by examiner

METHODS AND SYSTEMS FOR MONITORING INTRABODY TISSUES

RELATED APPLICATIONS

This application is a continuation of U.S. patent application Ser. No. 13/254,852, filed on Sep. 5, 2011, which is a National Phase of PCT Patent Application No. PCT/IL2010/000182 having International Filing Date of Mar. 4, 2010, which claims the benefit of priority of U.S. Provisional Patent Application No. 61/157,261 filed on Mar. 4, 2009.

U.S. patent application Ser. No. 13/254,852 is also a continuation-in-part of U.S. patent application Ser. No. 12/676,381 filed on May 6, 2010, which is a National Phase of PCT Patent Application No. PCT/IL2008/001199 having International Filing Date of Sep. 4, 2008, which claims the benefit of priority of U.S. Provisional Patent Application Nos. 60/969,963, 60/969,965, and 60/969,966, all filed on Sep. 5, 2007.

U.S. Patent Application No. 13/254,852 is also a continuation-in-part of U.S. patent application Ser. No. 12/676,385 filed on of Jul. 1, 2010, which is a National Phase of PCT Patent Application No. PCT/IL2008/001198 having International Filing Date of Sep. 4, 2008, which claims the benefit of priority of U.S. Provisional Patent Application Nos. 60/969,963, 60/969,965, and 60/969,966, all filed on Sep. 5, 2007.

The contents of the above applications are all incorporated by reference as if fully set forth herein in their entirety.

FIELD AND BACKGROUND OF THE INVENTION

The present invention, in some embodiments thereof, relates to a system and a method for monitoring a pathological condition of a patient and, more particularly, but not exclusively, to a system and a method for monitoring pathological and physiological condition of a user using EM radiation.

During the last years, various methods and devices have been developed for diagnosing intrabody tissues using electromagnetic (EM) radiation. For example, U.S. Pat. No. 6,061,589, published on Sep. 5, 2000 describes a microwave antenna for use in a system for detecting an incipient tumor in living tissue such as that of a human breast in accordance with differences in relative dielectric characteristics. In the system a generator produces a non-ionizing electromagnetic input wave of preselected frequency, usually exceeding three gigahertz, and that input wave is used to irradiate a discrete volume in the living tissue with a non-ionizing electromagnetic wave. The illumination location is shifted in a predetermined scanning pattern. Scattered signal returns from the living tissue are collected and processed to segregate skin tissue scatter and to develop a segregated backscatter or return wave signal; that segregated signal, in turn, is employed to detect any anomaly indicative of the presence of a tumor or other abnormality in the scanned living tissue.

In another example, U.S. Pat. No. 6,919,838 published on Jul. 19, 2005, describes a scanner or imager that employs a plurality of microwave transmitters that emit a multiplicity of pulses, which are received by a plurality of receivers. An object or person positioned between the transmitters and receivers can be scanned and subsequently imaged in extreme detail, due to the broad spectral content of the pulses.

International Patent Application Number IL2008/001199, filed on Sep. 4, 2008, which is incorporated herein by reference, describes a method for monitoring thoracic tissue. The method comprises intercepting electromagnetic (EM) radiation from thoracic tissue of a patient in continuous or intermittent EM radiation sessions during a period of at least 24 hours, detecting dielectric coefficient of the thoracic tissue by analyzing respective intercepted EM radiations, and outputting a notification indicating the change. The intercepted EM radiationis changed as an outcome of physiological processes as well as thoracic movements which occur during the period. The intercepted EM radiation may be reflections of EM radiation transmitted toward the thoracic tissue, EM radiation passing through the thoracic tissue, and/or EM radiation scatter from the thoracic tissue.

International Patent Application Number IL2008/001198, filed on Sep. 4, 2008, which is incorporated herein by reference, describes a wearable monitoring device for monitoring at least one biological parameter of an internal tissue of an ambulatory user. The wearable monitoring device comprises at least one transducer configured for EM radiation to the internal tissue and intercepting EM radiation therefrom in a plurality of continuous or intermittent EM radiation sessions during at least 24 hours, a processing unit configured for analyzing respective intercepted EM radiation and identifying a change in the at least one biological parameter accordingly, a reporting unit configured for generating a report according to the change, and a housing for containing the at least one transducer, the reporting unit, and the processing unit, the housing being configured for being disposed on the body of the ambulatory user.

SUMMARY OF THE INVENTION

According to some embodiments of the present invention there is provided a method for monitoring an intrabody region of a patient. The method comprises intercepting a plurality of electromagnetic (EM) radiations from the intrabody region in a plurality of EM radiation sessions during a period of at least 6 hours, calculating a dielectric related change of the intrabody region by analyzing the plurality of electromagnetic radiations, detecting a physiological pattern according to the dielectric related change, and outputting a notification indicating the physiological pattern.

Optionally, the patient is an ambulatory patient and the intercepting being performed during a period of at least 12 hours.

Optionally, the dielectric related change reflects a change in a plurality of properties of the intrabody region.

More optionally, the plurality of properties comprises a member of a group consisting of a density, a size, a shape, and a concentration of fluids.

Optionally, the calculating comprising registering EM radiations intercepted during a first of the plurality of EM radiation sessions with a second of the plurality of EM radiation sessions.

Optionally, the intrabody region comprises a cancerous tissue and the physiological pattern is a reaction of the cancerous tissue to an oncological therapy.

More optionally, the physiological pattern is a reaction of the cancerous tissue to a member selected from a group consisting of: a chemotherapy cycle, a biologic treatment, an antineovascular agent and a radiation treatment.

Optionally, the physiological pattern is a reaction of the intrabody region to a medical operation performed on the patient.

Optionally, the method further comprises automatically dispensing a medical substance into the patient according to the physiological pattern.

Optionally, the notification comprises a recommendation to a medical procedure according to the physiological pattern.

More optionally, the medical procedure comprising a member of a group consisting of: a dosage of a medical agent, a dispensing of a medical substance, a radiation protocol, a rehabilitation process, and a diagnosis procedure.

Optionally, the detecting is performed by combining at least one biological parameter of the patient with the dielectric related change for detecting the physiological pattern.

More optionally, wherein the at least one biological parameter comprises a member of a group consisting of: an electrocardiogram (ECG) signal, a temperature, a body orientation, a body acceleration, a hemodynamic parameter, $CO_2$ saturation, $O_2$ saturation, a pulse wave and a blood pressure.

Optionally, the detecting is performed by combining at least one diagnostic result related to the intrabody region with the dielectric related change for detecting the physiological pattern.

Optionally, the intrabody region is a pulmonary tissue and the notification is indicative of atelectasis.

Optionally, the physiological pattern is an expected dielectric related change indicative of a blood accumulation in an intrabody tissue.

Optionally, the intrabody region comprises a cerebral tissue and the physiological pattern is indicative of a cerebral edema.

Optionally, the patient is a non compliant patient selected from a group consisting of an intensive care patient, a new-born suffering from respiratory distress syndrome, a patient under general anesthesia, a child patient and a toddler patient.

Optionally, the method further comprises using an imaging modality for imaging the intrabody tissue and registering the monitoring device with the imaging for performing the intercepting.

Optionally, the method further comprises using an imaging modality for detecting at least one characteristic of the intrabody tissue, the detecting is performed according to the at least one characteristic.

Optionally, the physiological pattern based on a reference parameter extracted from a modality imaging the intrabody region.

Optionally, the patient is an intubated patient and the intrabody region comprises a pulmonary tissue.

Optionally, the patient is an anesthetized patient.

According to some embodiments of the present invention there is provided a method for monitoring an intrabody region. The method comprises performing stress ergometry on a patient according to a stress examination test, intercepting a plurality of electromagnetic (EM) radiations from the at least one intrabody region of the patient in at least one EM radiation session, calculating a dielectric related change of the at least one intrabody region by analyzing the plurality of electromagnetic radiations, detecting a physiological pattern according to the dielectric related change, and outputting a notification indicating the physiological pattern.

According to some embodiments of the present invention there is provided a monitoring device for detecting a physiological pattern of an intrabody region. The monitoring device comprises a probe configured for intercepting plurality of electromagnetic (EM) radiations from the intrabody region of a patient, a processing unit calculating a dielectric related change of the intrabody region by analyzing the plurality of EM radiations and detecting a physiological pattern according to the dielectric related change, and an output unit configured for outputting a message indicating the physiological pattern. The probe and the processing unit are configured for respectively performing the intercepting and the analyzing in a plurality of EM radiation sessions during a period of at least 6 hours.

Optionally, the output unit is connected to a medical device providing a treatment to the patient, the medical device being configured for providing the treatment according to the message.

More optionally, the medical device comprises a respiration machine being configured to apply artificial respiration to the patient, the respiration machine being configured for adjusting the artificial respiration according to the message.

According to some embodiments of the present invention there is provided a monitoring device for detecting a physiological pattern of an intrabody region. The monitoring device comprises at least one probe configured for intercepting a plurality of electromagnetic (EM) radiations from an intrabody region of a patient and from a reference intrabody region of the patient, at least one processing unit configured for calculating a dielectric related change in the intrabody region and a reference dielectric related change in the reference intrabody region according to the plurality of EM radiations and identifying a physiological pattern according to a combination of the dielectric related change and reference dielectric related change, and an output unit configured for outputting a notification indicating the physiological pattern.

According to some embodiments of the present invention there is provided a method for monitoring a physiological pattern of an intrabody region. The method comprises fixating a monitoring device in relation to a body of a non-compliant patient, intercepting plurality of electromagnetic (EM) radiations from the at least one intrabody region of the patient in at least one EM radiation session, calculating a dielectric related change of the at least one intrabody region by analyzing the plurality of EM radiations, detecting a physiological pattern according to the dielectric related change, and outputting a notification indicating the physiological pattern.

Optionally, the intercepting is performed while the patient is transported.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volitile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DESCRIPTION OF EMBODIMENTS OF THE INVENTION

Figure 1:
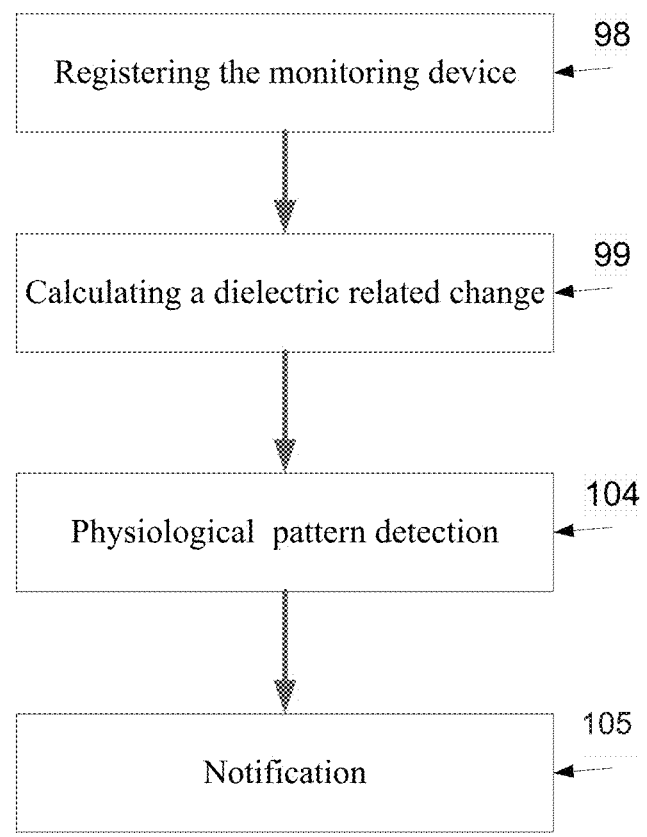
FIG. 1 is a flowchart of a method for monitoring an intrabody tissue of a patient during a monitoring period of more than 6 hours, according to some embodiments of the present invention.

The present invention, in some embodiments thereof, relates to a system and a method for monitoring pathological condition of a patient and, more particularly, but not exclusively, to a system and a method for monitoring pathological and physiological condition of a user using EM radiation.

According to some embodiments of the present invention there is provided a system and a method for detecting a physiological pattern, such as pathological pattern and non-pathological pattern of one or more intrabody tissues, for example from a selected region, by monitoring dielectric related changes thereof.

A dielectric property or coefficient of a material describes its interaction with EM fields; it is represented by a frequency dependent complex number describing the electrical permittivity and the conductivity of the material, as known in the art. In this patent and the International Patent Applications Numbers IL2008/001198 and IL2008/001199, filed on Sep. 4, 2008 which are incorporated herein by reference, dielectric coefficient refers to complex dielectric coefficient representing both the permittivity and conductivity characteristics of the material. Different intrabody regions include one or more tissues which are characterized by different complex dielectric coefficients referring the permittivity and conductivity. The dielectric parameters of tissues have been measured, researched and organized by Gabriel at el. and serve as a golden standard. For example, a tissues containing high water content like muscle are characterized by a relatively high complex dielectric coefficient in both its real and imaginary part, where dry tissues like fat have low relative complex dielectric coefficient in both its real and imaginary parts. The complex dielectric coefficient of an intrabody region is affected greatly by its fluid content. For example, a normal fat tissue with relatively low fluid content is characterized by a relatively low dielectric coefficient with relative permittivity of 5.44 and conductivity of 0.0535 S/m, while a muscle tissue is characterized by higher blood content and relatively high dielectric coefficient, relative permittivity of 54.8 and conductivity of 0.978 S/m.

A dielectric related property of a tissue or region means a property that is related to the dielectric property thereof. Such a dielectric related property affects the electro-magnetic radiation which interact with the tissue that incident upon the related region; changes in dielectric related properties of a region may change any one or more of the following: the amplitude of the EM radiation which is intercepted after interacting with the tissue, delay effects on the intercepted EM radiation, phase of the intercepted EM radiation, frequency content of the intercepted EM radiation, dispersion of the intercepted EM radiation and/or any similar properties of the intercepted EM radiation. The intercepted EM radiation may be reflections of EM radiation transmitted toward the tissue, EM radiation passing through the tissue, and/or EM radiation scattered from the tissue.

A dielectric related change can result from a change in one or more dielectric properties of specific tissues within an intrabody region as well as changes in the configuration of tissues within the region. For example, in case of a change in the intrabody region, such as when blood fills the tissue parenchyma, a change in the dielectric coefficient of the region is expected. Similarly, an ischemic region within a tissue will change its properties to fibrotic tissue reflected by lower dielectric coefficient. In another example, a region may have a dielectric related change as a result of a cancerous tumor within the region growing in size or becoming more vascularized.

As used herein, a physiological pattern means an estimated change in one or more dielectric properties of a respective intrabody region comprising one or more tissues, such as a connective tissue and a tissue of a bone, a muscle, a joint, a cartilage, and/or one or more internal organs, for example the lungs, the kidneys, and the brain. Optionally, the physiological pattern may be a pathological pattern of an expected change in an intrabody region that occurs in response to an operation, a treatment, a medical condition, and/or pathology. Additionally or alternatively, the physiological pattern may be a non-pathological pattern, such as an expected change that is triggered by a medical treatment, such as an oncological treatment, such as chemotherapy, an expected reaction to a medical substance, and an expected reaction to a physical exercise. The change of the physiological state of a region is monitored over the measurement period resulting in a dynamic pattern. The physiological state may be defined by various parameters describing different aspects of the physiological state. Thus, the physiological pattern may include the time course of the different parameters over time.

The method comprises intercepting a plurality of electromagnetic (EM) radiations from the one or more intrabody tissues of a patient in a plurality of continuous or intermittent EM radiation sessions during a period of 6 hours or more. The plurality of EM radiations sessions may include the transmitting of EM radiation toward the intrabody region, the transmitting of EM radiation which interacts with the intrabody region, the intercepting of reflections of EM radiation from the intrabody region, the intercepting of EM radiation that interacts with one or more bodily tissue and/or the detection of responses of EM radiation to the intrabody region. Then, a dielectric related change is calculated by analyzing the changes in the intercepted EM waves during the EM radiation sessions and between radiation sessions over the monitoring period. The dielectric related change allows detecting a physiological pattern of the intrabody tissue and outputting a notification indicating the pathological pattern to the patient or to a caretaker thereof.

The monitoring and assessment of the dielectric related changes of intrabody regions in hospitalized and unhospitalized patient allows monitoring physiological and anatomical changes in the intrabody region, for example for detecting a growth and/or reduction in the size of a tumor. By detecting such changes, which are indicative of pathological patterns, a more effective and safe treatment may be given. For example, a titration of drug treatment may be adjusted according to the type, rate, and/or intensity of the detected pathological pattern. Another example is a situation in which the definitive treatment of the tumor is surgical but the tumor is too large or developed in a difficult location for removal. In such cases a, neoadjuvant chemotherapy is necessary to reduce the tumor size. The monitoring allows notifying a caretaker and/or the patient when to proceed with the surgery. In another example, an administration of excess drugs may be avoided. It should be noted that by using such a non invasive procedure, other monitoring procedures, which are usually more risky and/or incurring exposure to ionizing radiation, may be avoided. In addition, such monitoring may allow generating an indication that assists in a hospital discharge timing decision.

In other embodiments of the present invention, there is provided a system and a method for monitoring dielectric related changes of one or more intrabody tissues during a stress examination. In such a manner, the accumulation of fluids in the monitored intrabody tissues may be detected during the stress phase, improving the sensitivity and specificity of the stress examination to pathological states. In other embodiments of the present invention, there is provided a system and a method for monitoring dielectric related changes of one or more intrabody tissues of low or non compliant patients and/or patients which are transported to a medical center to receive a medical care.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Reference is now made to FIG. 1, which is a schematic illustration of a method 100 for monitoring an intrabody region of a patient during a monitoring period of more than 6 hours by analyzing dielectric related properties thereof, according to some embodiments of the present invention.

As shown at 99, the method is based on detecting a dielectric related change 99 in the EM properties of the intrabody region. The dielectric related change 99 is detected by evaluating the dielectric related properties of the intrabody region in a plurality of EM radiation sessions which are held during a period of 6 hours or more. The monitoring may be adjusted to take into account changes in the dielectric related properties of the monitored intrabody region, such as changes which occur as an outcome of a reaction to a medical treatment, a change of physiological state and body movements.

Optionally, the monitoring is performed by a wearable monitoring device, a probe and/or by a device having wearable probes, for example similar to the devices which are described in International Patent Applications Numbers IL2008/001198 and IL2008/001199, filed on Sep. 4, 2008, which are incorporated herein by reference. For brevity, each one of these devices may be referred to herein as a monitoring device or a probe.

In such embodiments, as shown at 98, the locations of the intrabody regions and/or their effect on the intercepted EM radiation may be identified before the monitoring begins in a process which may be referred to herein as a registration process. Optionally, the registration process is performed with respect to an imaging modality such as, a computerized tomography (CT), a magnetic resonance imager (MRI), a positron emission tomography (PET)-CT, and/or an EM tomography device that is used to identify the location of the intrabody region so that the monitoring device may be positioned and/or diverted to intercept the EM radiation therefrom. For example, the imaging modalities may be used for identifying the location of a cancerous tissue, such as a tumor, for example a hepatic tumor and a chest tumor. The identification allows, inter alia, the positioning of the monitoring device and/or the probe thereof in a manner that the EM radiation is emitted toward the intrabody region. In addition, the identification allows initializing a number of base values for calibrating the analysis that is described in relation to 104 in FIG. 1. The identification may be similarly performed using an imaging modality use in association with a therapeutic modality such a cryoprobe or heatprobe. Optionally, the registration process is performed using known registration processes and known imaging modalities for registration of specific intrabody regions, such as tumors, cerebral tissues, and/or bleeding tissues.

Optionally, the monitoring device, which is disposed or attached to the body, performs the EM radiation sessions during an imaging process which is performed by either of the abovementioned imaging modalities. Such EM radiation sessions allow a definite position of the monitoring device in relation to a region of interest (ROI) that includes the intrabody region and defined by the imaging modalities. Optionally, the anatomical reconstruction of the ROI and its surrounding tissue are forwarded to the monitoring device and allow calculating an expected signal subject to expected changes of the physiological state of the intrabody region. Finite element methods may incorporate this anatomical information to compute the reflections and/or otherwise affected EM waves which are intercepted during the EM sessions. For brevity, a reflection means any EM radiation which interacts with an intrabody region, such as the ROI, for example EM radiation which are transmitted via the intrabody region, scattered from the intrabody region, and/or reflected from the intrabody region.

Figure 3:
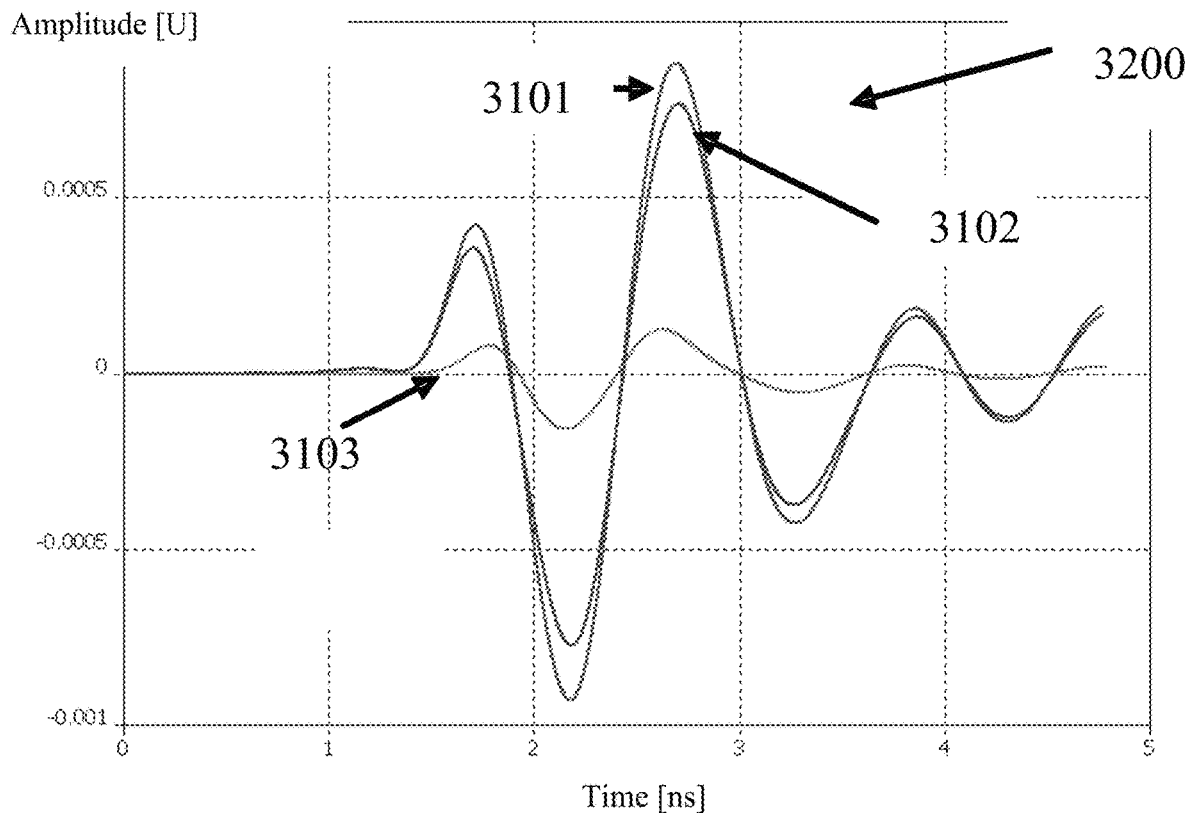
FIG. 3 is a graph of a waveform intercepted from a simulated tumor after a dielectric related property thereof has been changed.
Figure 4:
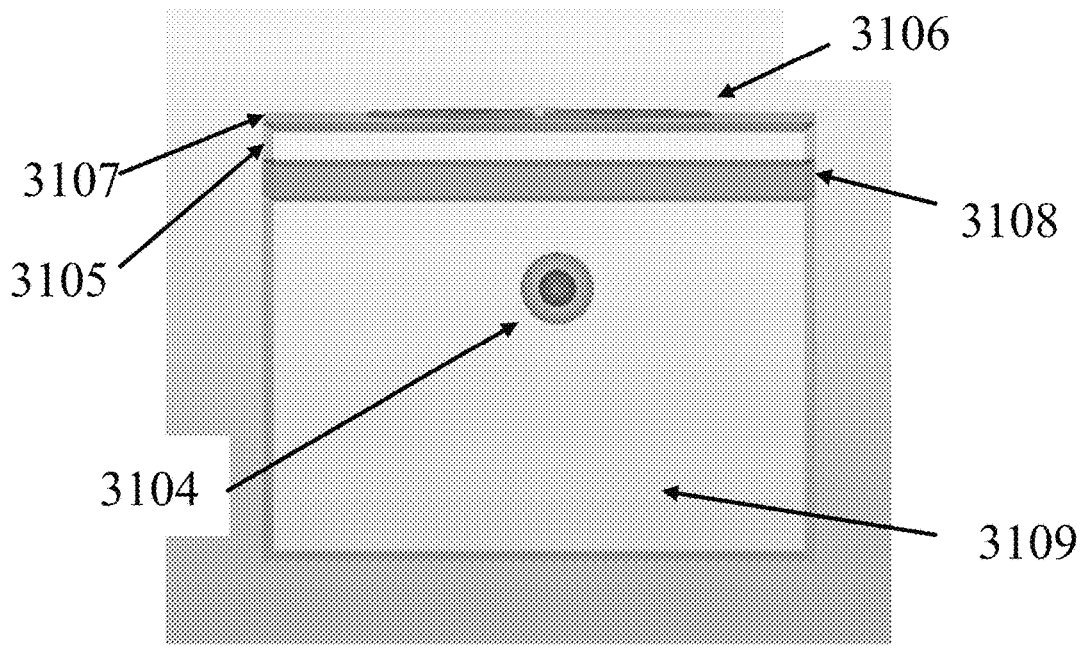
FIG. 4 is a schematic illustration of an exemplary intrabody region that surrounds the simulated tumor of FIG. 3.

In addition, the effects of the physiological changes may be simulated to produce an expected signal which is matched when detected and notified. For example, a hepatic tumor may shrink as a result of chemotherapy, for instance go through a tumor remission. A computerized model of the entire EM irradiated region may calculate the resultant signal, and in case of a shrinkage of the tumor may be simulated and produce an expected signal, used for detection of such a state. For example, reference is now also made to FIGS. 3 and 4 which are, respectively, a graph of waveforms intercepted after a dielectric related property of a simulated intrabody region, such as a tumor has been changed and a schematic illustration of an exemplary intrabody region that surrounds the tumor. FIGS. 3 and 4 depict a three dimensional finite element simulation which has been conducted with realistic anatomical dimensions as may be provided by an imaging modality, such as CT, MRI and PET. In the simulation, a lung tumor 3104 in the lung 3109, below a layer of skin 3107, a layer of fat 3105, and a layer of muscle 3108. The simulation simulated an increase and a decrease in the tumor's size, as an estimated consequence of ineffective and effective treatment. The simulation included a pulse transmitted from an EM transducer 3106, such as the one described below, width equal to about 350 picoseconds (ps). In the simulation, the pulse propagated through a 3 mm layer of skin 3107, 10 mm layer of fat 3105, and 10mm layer of muscle 3108 into the lung 3109. The center of the tumor 3104 is 30 mm deep the lungs. During the simulation, the radius of the simulated tumor 3104 was increased to simulate an ineffective treatment and decreased to simulate an effective treatment. The tumor dielectric coefficient is relatively high due to estimated high blood content around the tumor. For example, its dielectric coefficient is close to that of the muscle. In particular, the simulation results, which are depicted in FIG. 3, show waveforms in the time domain representing the difference between the following reflections which are received from the tumor 3104: 3103 is waveform intercepted after the simulated tumor reducing from 5 mm to 0 mm, 3102 is waveform intercepted after a simulated tumor shrinks from a radius of 10 mm to a radius of 5 mm, and 3101 is waveform intercepted after a simulated tumor shrinks from 10 mm to 0 mm. The simulation explicitly exemplify how a dielectric related change shows that different changes in a dielectric related property, such as the size of the intrabody region, which is optionally a tumor, are distinguished from one another.

Optionally, the monitoring device is designed for monitoring dielectric related changes of the intrabody region of an ambulatory user, for example as described in Application Number IL2008/001198, filed on Sep. 4, 2008, which the content thereof is incorporated herein by reference. In such an embodiment, the monitoring device comprises at least one transducer for delivering EM radiation to the internal tissue and intercepting EM radiation therefrom in a plurality of EM radiation sessions during a period of at least 6 hours, a processing unit configured for analyzing the intercepted EM radiation and identifying the presence or the absence of one or more pathological patterns accordingly, a reporting unit configured for generating a report according to changes in the intercepted EM radiation, and a housing for containing the at least one transducer, the reporting unit, and the processing unit. The monitoring device is capable of providing indications for proper disposing of the sensor on the patient body, or of providing indications for proper positioning of the apparatus with respect to a monitored region of interest (ROI) that includes the intrabody region, such that, the ROI is observed in a manner similar to the previous observations and such that the measurements and reconstructed properties of the ROI state may be compared with previous estimations from previous measurements. For the sake of the operation, the patient may be frequently monitored by standard imaging modalities for extracting of a range of ROI related parameters. These parameters are used for a calibration of the device. It should be noted that the monitoring device may interface with and/or integrate into other sensors, imaging modalities, treatment devices and information technology systems of different organizations, such as hospitals, caretaker clinics, long term care facilities, nursing homes, home care service providers, call centers, and the like. As used herein, a caretaker means a physician, a nurse, a family member, an affiliate, a medical center staff member, a call center, or any entity that manages and/or should have access to the specific information related to the medical condition of the monitored patient and/or a team of one or more of these caretakers.

Optionally, the identification of the location of the intrabody region, which is optionally a cancerous tissue, is identified using an imaging modality, according to a registration process. Optionally, the output of the registration process is a set of instructions that allow the patient or a caretaker to position a monitoring device, for example as defined below in relation to FIG. 8, to emit EM radiation and to capture the reflection thereof, for example as depicted in 101 and 102 of FIG. 2. Optionally, the registration process defines the location of a tumor in relation to well defined anatomical structures and/or fiduciary markers, such as specific markers which are attached to the patient. For example, if the intrabody region is located in the chest, the registration process may output positioning instructions by analyzing distances from specific ribs or from the chest vertebrae. Similarly, patches can be attached to the skin of the patients or guides could be drilled into the pelvis in case of prostate tumor so as to be used as fiduciary markers.

Additionally or alternatively, the output of the calibration process may include information about the current state of the intrabody region and/or region, optionally accounting for various parameters that are further characterized such as the density, the size, the shape, and the necrosis parameters. Optionally, these parameters may include EM sensor related information for example regarding the sensor absolute position and/or relative position to one or more intrabody regions, external-body objects and/or other sensors. Optionally, an intrabody region, such as a tumor, may be indentified by one or more imaging modalities, such as CT, PET and fluoroscopy. For example, if the intrabody region is a tumor, these modalities may provide information related thereto, such as the density the fluid content, the vascularization level, the effect of fibrosis, the functional and/or the metabolic properties of the cancerous tissue characterized by the blood supply may be provided and used for optimal calibration process performed by the system used in the forgoing monitoring. The updated physiological state is used for expecting some prognostic stages, either desired or not. For example, the monitoring device may be used for monitoring a patient treated for a lung cancer, at a stage of neovascularization. While receiving chemotherapy, it is expected that the treatment reduces the vascularization that leads to necrosis and later to shrinkage of the tumor and more fibrosis.

Figure 2:
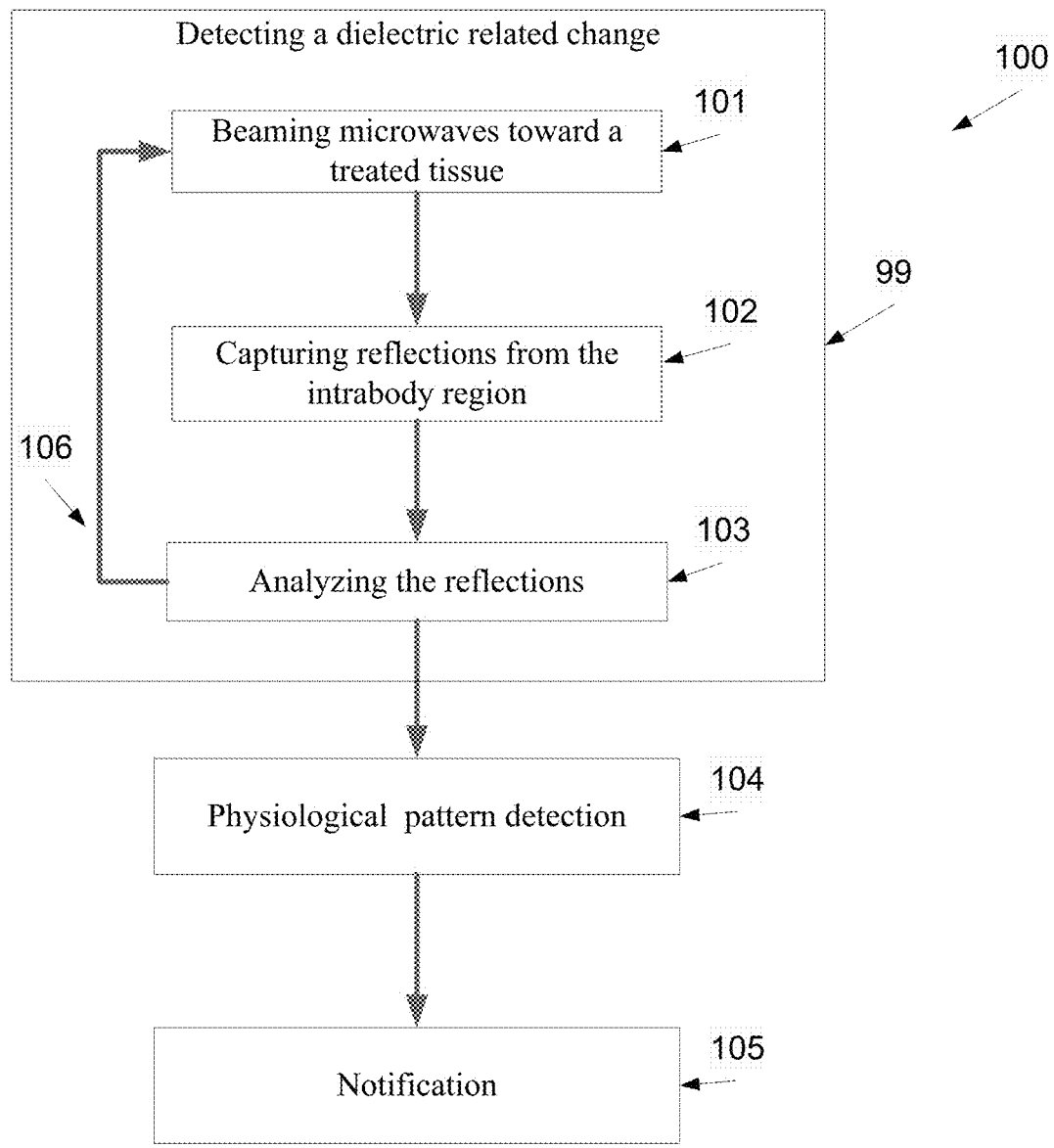
FIG. 2 is a flowchart of a method for monitoring an intrabody tissue of a patient by a plurality of EM radiation sessions, according to some embodiments of the present invention.

As depicted in 99, the positioning of the monitoring device allows detecting dielectric related changes in intrabody region. The dielectric related changes are optionally detected by a plurality of EM radiation sessions which are performed during a period of 6, 12, 24, 48, 72 hours, intermediate or longer periods and/or during a period during which the patient's medical condition is to be monitored, for example during a stress examination and/or a transportation for medical care, as described below. Reference is now also made to FIG. 2, which is a flowchart of a method for monitoring an intrabody region, according to some embodiments of the present invention. Optionally, blocks 98, 99 and 104-105 are as depicted in FIG. 1. However, FIG. 2 further depicts blocks 101-103 that depict one of the EM radiation sessions.

First, as shown at 101, EM radiation is beamed from a monitoring device, for example in a similar manner to describe in International Patent Applications Numbers IL2008/001198 and IL2008/001199, filed on Sep. 4, 2008 which are incorporated herein by reference.

Then, as shown at 102, a reflection of the beamed EM radiation is captured. In some embodiments of the present invention, the beamed EM radiation is in the range of 3 MHz to 60 GHz, inclusive. In such a mode, time gating may be used for focusing on a specific reflection, as further detailed in International Patent Applications Numbers IL2008/001198 and IL2008/001199, filed on Sep. 4, 2008 which are incorporated herein by reference. The shape of the pulse may be generated using different shaping techniques. It should be noted that though this document mostly refer to an analysis that is based on the interception of reflections of the EM radiation from the intrabody region, an analysis which is based on EM radiation that is intercepted after it passed through the intrabody region may be performed additionally or alternatively.

In some embodiments of the present invention, as further described below, the beamed EM radiation is narrowband waves, optionally modulated, optionally in a predefined range of frequency bands, as described in International Patent Applications Numbers IL2008/001198 and IL2008/001199, filed on Sep. 4, 2008 which are incorporated herein by reference.

In some embodiments of the present invention, sequential measurements are registered and only these measurements are compared to previous measurements taken at the same physiological state and posture. Methods for registering a position of the monitoring device with respect to a region of interest, for a detection of a posture, and a detection of similar physiological states, are described in International Patent Applications Numbers IL2008/001198 and IL2008/001199, filed on Sep. 4, 2008 which are incorporated herein by reference.

Now, as shown at 102, a reflection of the beamed EM radiation is captured. As described above, a change in the intrabody region is detected by detecting changes in the dielectric related properties thereof, for example as described below.

After the reflected EM radiation has been captured, analysis of the captured signals, for example as shown at 103, is performed. The analysis may take into account the posture of the user and/or the placement of the monitoring device that is designed for receiving the reflection from the monitored tissue. In addition, it may use two measurements acquired in at distinct physiological state to compute a differential signal, for example as described below and in International Patent Applications Numbers IL2008/001198 and IL2008/001199, filed on Sep. 4, 2008 which are incorporated herein by reference.

Optionally, as shown at 106, blocks 101-103 are repeated in a plurality of transmission and interception sessions, referred to herein as EM radiation sessions, for gathering continuous and/or discrete signals indicative of dielectric related changes in the intrabody region. These dielectric related changes may be indicative to various pathological patterns and/or pathological tissue behaviors, for example as described below. For example, in each EM radiation session, a dielectric related property is measured during one or more intervals. Optionally, each EM radiation session lasts between few pico-seconds and few hours, optionally minutes. In use, the EM radiation which is intercepted during a number of EM radiation sessions allow calculating the dielectric related change which may be indicative of a change of fluid content within a biological tissue and/or region. Such a dielectric related change may reflect for example a bodily heat change, a necrosis, a fibrosis, and/or a change in the blood supply to the monitored intrabody region.

Multiple EM radiation sessions measured might be required for monitoring changes over long periods of time. In such cases the measurements comparing the intrabody detected parameters requires that the patient will be in a certain posture, physiological state and placed in a specific position relative to the measured intrabody region. Different mechanisms described in this patent the International Patent Applications Numbers IL2008/001198 and IL2008/001199, filed on Sep. 4, 2008 which are incorporated herein by reference, describe the posture detector, physiological state detector, registration and calibration mechanism essential to deal with changes over time of the patient.

The dielectric related change may be calculated by matching one or more dielectric related properties from one or more EM radiation sessions. Optionally, the dielectric related change reflects a pattern of one or more dielectric related properties which are recorded during a period of 1, 2, 4, 6, 8, 10, 12 and 24 hours, days, weeks, and/or months. For example, a user may position the EM probe to monitor the dielectric related properties of the intrabody region every 1, 2, 4, 6, 8, 10, 12 and 24 hours, days, weeks, and/or months and to calculate accordingly a dielectric related change. It should be noted that the probe may include one or more transducers for transmitting and intercepting the EM radiation and/or separate one or more transmitters and/ one or more receivers. Optionally, the transducers, receivers, and/ or transmitters are located in proximity to one another, for example one the same plane and/or in the same housing. Optionally, the transducers, receivers, and/or transmitters are positioned one in front of the other, allowing the reception of EM radiation that pass through the intrabody region.

As shown at 104, the dielectric related change allows calculating medical indices of interest, which are optionally based on physiological, anatomical and/or clinical parameters. The medical indices of interest may be used for detecting and/or evaluating physiological patterns which are indicative of normal and/or pathological tissue behaviors of the monitored intrabody region. Such an evaluation may be performed by comparing measured dielectric related changes to expected and/or estimated values of dielectric related changes in various conditions. This information may be compared and evaluated with respect to biological parameters, such as an electrocardiogram (ECG) signal, a temperature, a body orientation, a body acceleration, a hemodynamic parameter, $CO_2$ saturation, $O_2$ saturation, a pulse wave and a blood pressure and/or vital signs estimation, such as the heart rate, and breathing, for example as described in International Patent Applications Numbers IL2008/001198 and IL2008/001199, filed on Sep. 4, 2008, which are incorporated herein by reference.

In some embodiments of the present invention, characteristics, such as a change in a position, a size, a configuration and/or a state of an intrabody region and/or region, for example an operated tissue, a preoperated tissue, a postoperated tissue, cancerous tissue, such as a tumor, a change of intubation fixation, and a traumatized tissue, such as a tissue damaged or otherwise effected by a traumatic brain injury, are detected and/or measured by analyzing the dielectric related change in the intrabody region. The change, which may indicate a size growth and/or size reduction and/or change of tissue concentration within a region and/or change of fluid content and/or change of the composition and/or configuration of tissues in the intrabody region may be detected by analyzing changes in the reflected EM which are caused by changes to the dielectric related properties of the intrabody regions.

As shown at 105, the physiological patterns may be used in the analysis and may affect alert decisions made by the processing unit which may result in notifying the patient and/or medical caretaker. Such a notification may be used for alarming the patient and/or her medical caretaker with regard to an improvement and/or a decline in her status. Such alarming may reduce the time between the development of a certain health complication and a treatment thereafter.

Optionally, the notification provided in 105 includes a recommendation for a titration of a given treatment. Additionally or alternately, the recommendation includes a predetermined accepted range which matches the expected risk to patient. Similarly, the recommendation may include a change of a chemotherapy protocol as elaborated below. Additionally or alternatively, the notification is replaced with a message, such as a set of instructions to a medical treatment device, such as a medical substance dispenser and/or a respiration machine. For example, the set of instruction control adjust, and/or define a range for a medicament dispense and/or for configuring and/or reconfiguring parameters of a respiration machine. In use, the output of the monitoring device may be forwarded to the medical treatment device through a communication channel. Optionally, the processing of the EM interceptions and the analysis thereof is integrated within the medical treatment device. In such a manner, a medical treatment device, such as a respiration machine and a medical substance dispenser may be integrated with a probe for monitoring dielectric related changes, for example as described herein.

In some embodiments of the present invention, the analysis allows calculating a clinical state or change thereof of a patient based on an integrative index. The clinical state or change thereof is determined based on an analysis of a combination of the physiological patterns and/or the physiological patterns' change rate and/or biological parameters such as an electrocardiogram (ECG) signals, a temperature, a body orientation, a body acceleration, a hemodynamic parameter, $CO_2$ saturation, $O_2$ saturation, a pulse wave and a blood pressure and/or vital signs and/or detected trends of vital signs which are estimated based on analysis of the reflected EM radiation and/or other medical sensors, such as electrocardiogram (ECG), myogram (EMG), an ultrasound transducer, a pulse oximeter, a blood pressure sensor, a tiltmeter, an accelerometer, and coagulometer. The integrative index is optionally scaled and/or color coded to provide intuitive follow-up of the clinical status of the patient. Optionally, the monitoring device includes an adjustment unit for receiving adjustment information related to the monitored patient from the medical sensors. In such an embodiment the processing unit is configured for calculating the clinical state or change thereof according to the adjustment information.

Optionally, the monitoring device has a set up mode and a sequential monitoring mode. In use, the aforementioned registration process is performed during the set up mode, for example based on anatomical information as well as the physiological state of the ROI that is characterized by the various biological parameters.

Additionally or alternatively, the patient or the caretaker, at the set-up mode, may define specific events, characterized by predefined changes, for notifications. For example, the caretaker may define an urgent notification in case of abrupt changes in the rate of tumor diminution or a detection of a sudden bleeding. For example, the caretaker or the patient may define alerts to changes such as an increase of more than 20% in the size of an intrabody region, such as a tumor, or a bleeding of more then 100 cc. Alternatively, the monitoring device may be configured for providing a notification, such as an alert, if a reduction in the necrosis process, an initiation of bleeding, and/or a change of the rate of the bleeding is detected.

The setup process may be repeated every time imaging of another modality is conducted, for refining the registration and calibration.

In the sequential monitoring mode, the aforementioned EM radiation sessions are performed. The dielectric related changes, which are detected during the EM radiation sessions, may be used for estimating a relative change for characterizing the current status of the intrabody tissue.

Oncological Monitoring

According to some embodiments of the present invention, the intrabody region is a cancerous tissue, such as a tumor, and the dielectric related changes are indicative of changes in the cancerous tissue. The method allows monitoring the tumor's response to an oncological treatment, for example radiations, chemotherapy, pre-radiation chemotherapy, pre-surgical chemotherapy (neoadjuvant therapy), hormonal therapy, and anti angiogenesis therapies, on an hourly, daily, and/or weekly or and/or other periodic basis. Some therapies have an estimated affect on the intrabody region. In such an embodiment, detected pathological patterns, for example these detected in 104, may reflect a change in a tumor size, either regression or growth, a change in the composition of a tumor, for example in the necrosis percentage thereof, a change in the vascular density of the tumor, or a change in the bleeding rate the tumor may have caused, a change in morphology of a tumor which is affected by the amount of blood therein, and/or a change in the blood supply in the vicinity of the tumor. For example, see Juweid M E: *Positron-Emission Tomography and Assessment of Cancer Therapy. N Engl J Med* 2006; 354:496-507I and Schiller J. H *Noninvasive Monitoring of Tumors: N Engl J Med* 359: 418, Jul. 24, 2008, which are incorporated herein by reference.

Figure 5:
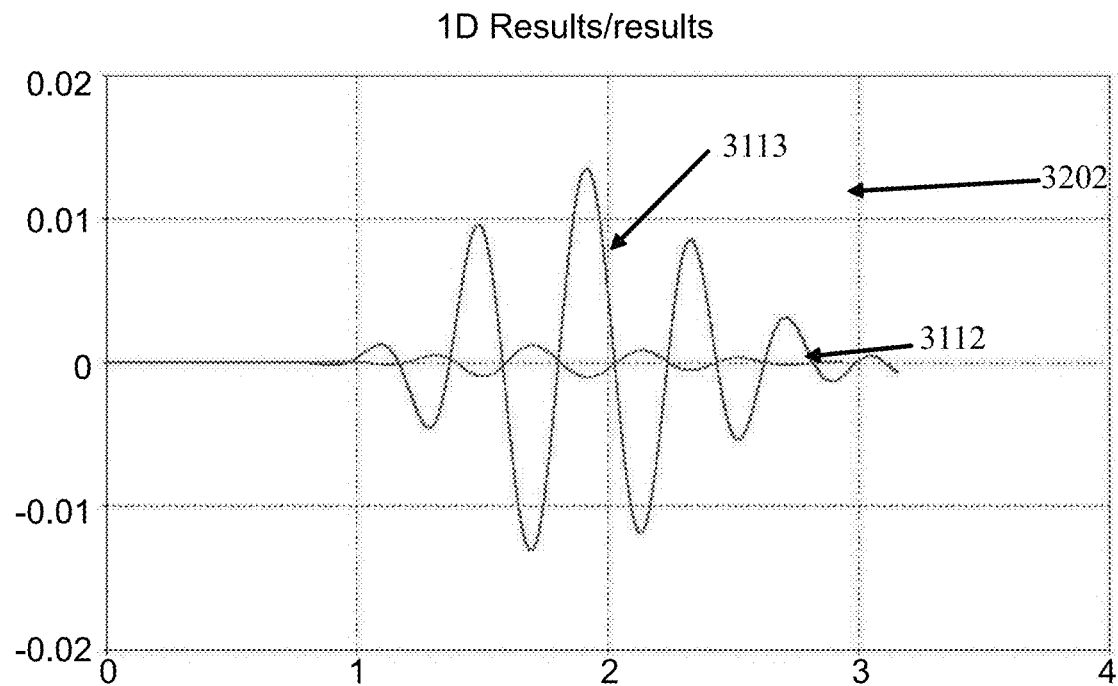
FIG. 5 is a graph of waveforms intercepted after a plurality of dielectric related properties of a simulated intrabody region, such as a bone tumor, that has been changed.
Figure 6:
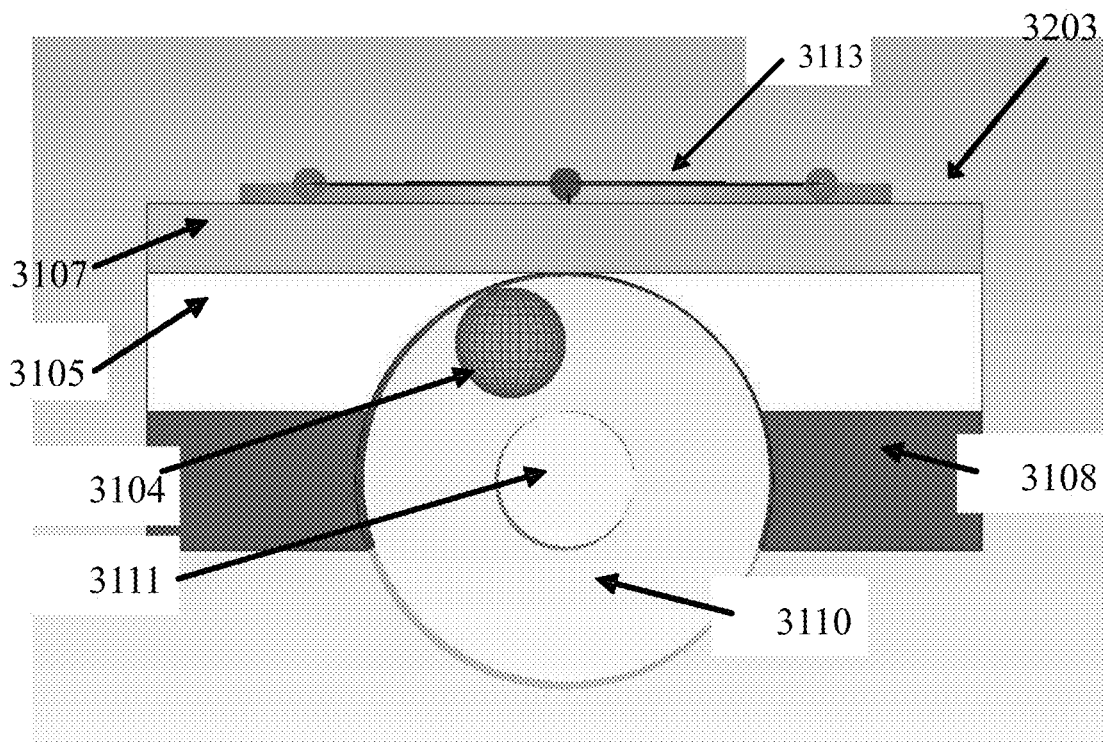
FIG. 6 is a schematic illustration of an exemplary intrabody region that surrounds the bone tumor depicted in FIG. 5.

As described above, the monitoring device may be used for providing a physiological pattern based on a plurality of dielectric related properties. Reference is now also made to FIGS. 5 and 6 which are, respectively, a graph of waveforms intercepted after a plurality of dielectric related properties of a simulated intrabody region, such as a bone tumor, which have been changed and a schematic illustration of an exemplary intrabody region that surrounds the bone tumor.

FIGS. 5 and 6 depicts the outcome of a simulation made using an EM transducer, is demonstrated in the following simulation. FIG. 5 depicts a differential waveform from a bone tumor 3202. The simulated model is described in 3203 and based on simulated anatomical information that may be provided by one or more imaging modalities, such as CT or MRI, for a bone tumor diagnosis. Two possible physiological effects were simulated, usually relevant in different stages of the bone tumor, for example shrinkage of a dimension and a change of bone tumor content due to necrotic processes while preserving its dimension. In particular, the simulation emulates an intercepted radiation which is transmitted from the transducer 3113 propagates through a 5 mm layer of skin 3107 into a layer of cortical outer bone 3110, which is surrounded by a 10 mm layer of fat 3105 and a 10 mm layer of muscle 3108, and reflected from the bone tumor 3104. The bone radius is 15 mm and the center of the bone includes a bone marrow tissue 3111 with 5 mm radius. The differential waveforms presented in FIG. 5 show the difference in the reflection. Waveform 3112 depicts shrinkage of a simulated bone tumor from 8 mm high blood content bone tumor to a 4 mm high blood content bone tumor. Waveform 3113 depicts a change in the blood content in a simulated bone tumor from high to low, where its dimensions of the simulated bone tumor remain the same, 4 mm radius. These results exemplify that different changes in the size or the shape of an intrabody region can be distinguished by identifying different dielectric related changes.

In such an embodiment, the notification 105 may be generated to indicate whether the chemotherapy has a beneficial and/or a detrimental effect on the cancerous tissue and optionally to what degree.

For example, the notification may be used for adjusting a titration process. In such an embodiment, the concentration of a medical substance which is given during the therapy is determined according to the notification. Optionally, the concentration of the medical substance is determined manually. In such an embodiment the caretaker or the patient prepares a medicament with a concentration which is selected according the notification. Optionally, the notification includes a concentration recommendation. Additionally or alternatively, the concentration of the medical substance is determined automatically, for example by a dosage unit that receives the notification. Such an automatic preparation allows automatic and/or manual dispensing of the medicament.

Optionally, the dielectric related changes are used for selecting an appropriate medicament for the patient. Thus, tumor suppression by the medicament is contingent on the specific oncogenic pathway that drives tumor development. Such a monitoring mode enables early detection of adverse reactions to therapy such as post radiation or chemotherapy induced pneumonitis.

Optionally, the notification is an alarm generated if the dielectric related change is indicative of a deviation from the expected outcomes of a respective chemotherapy cycle or any identifiable stage of an oncological treatment. In such an embodiment, a different effect is detected in different chemotherapy cycles. In particular, a different dielectric related change is expected in different chemotherapy cycles. For example, the expected result of a therapy, such as chemotherapy, platinum, etoposide and/or avastin based therapy, which is applied to a cancerous tissue, such as a tumor, is expected to cause a tumor to undergo several changes in a number of consecutive chemotherapy cycles. During the first chemotherapy cycle, tumor cells die and the number of blood vessels which lead blood to the tumor diminishes. Then, during the following chemotherapy cycle, a necrosis is formed in the tumor. The necrosis causes a subsequent change in the density of the tumor and an eventual shrinkage in its size.

The expected and/or estimated dielectric related change that is associated with various chemotherapy cycles may be determined according to clinical experiments and/or a numerical simulation of the chemotherapy cycles in humans. Optionally, the expected and/or estimated dielectric related change is adjusted to the medical information that is related to the monitored patient, for example the gender, the height, the weight, the body mass index (BMI), and/or the pathology of the patient.

If the pathological patterns 104 indicate that the changes do not respectively occur during the respective chemotherapy cycles, the notification may indicate that the chemotherapy process has to be stopped, adjusted, and/or replaced with another therapy. For example, the patient and/or the caretaker may replace a chosen therapy, change a used dosage and/or change a medication protocol.

Optionally, if the measured dielectric related changes are not indicative of a change, such as an increase in the rate of tumor's diminution and/or if the dielectric related changes are indicative of a change in a slower rate than expected, the treating caretaker may be alarmed.

Optionally, the notification is forwarded, wirelessly or by cable to a central patient management unit, for example as described in International Patent Application Number IL2008/001199, filed on Sep. 4, 2008 which are incorporated herein by reference. In such an embodiment, the notifications may be sent without the intervention of the patient and may include the complete record of the treatment. Additionally or alternatively, the notification is forwarded for the presentation thereof on an external device such as a medical monitor, a smart phone, and/or personal digital assistant (PDA) of the patient and/or the caretaker.

Optionally, the notification comprises a recommendation to a specific change in the treatment protocol and/or instructions to perform certain analyses or diagnoses of the intrabody region. For example, in the current practice, if a tumor increases in size after two treatment courses lasting a minimum of 6 weeks, a change in protocol is recommended. Showing an increase in tumor size along time, may permit the caretaker to change the protocol earlier and avoid unnecessary toxicity. This is the case in hematologic tumor such as Non-Hodgkin's Lymphoma which is usually treated with a C.H.O.P based protocol, and the protocol is substituted if tumor growth during treatment is demonstrated. Another example applies to treatment of Hodgkin's Lymphoma in which the tumor increases with the first-line protocol such as doxorubicin containing ABVD regimen (doxorubicin, bleomycin, vinblastine dacarbazine).

As described above, the device may be used for monitoring cancerous tissues.

In such an embodiment, the notification may include one or more estimations pertaining to the benefits of a therapy such as radiation, chemotherapy or biologic therapy such as Tyrosine kinase inhibitors directed against the epidermal growth factor receptor (EGFR).

Optionally, the monitoring that is performed by the monitoring device is calibrated according to one or more physiological processes of the patient. For example, when monitoring a cancerous tissue that is located at the thorax, such as a tumor of lung cancer, the calibration is performed according to the breathing cycle of the patient, taking into account expected differences between the signals received during inhalation and the signals received during exhalation, for example as described in International Patent Applications Numbers IL2008/001198 and IL2008/001199, filed on Sep. 4, 2008 which are incorporated herein by reference.

The relative changes are analyzed with respect to the device configuration, calibration, thresholds and setup as provided by manufacturer presets and by the treating caretaker and proper notifications are sent to the patient and/or directly to the treating caretaker.

Post-operative Complications

According to some embodiments of the present invention, the intrabody region is a traumatized or potentially traumatized tissue, such as an operated tissue or a tissue which is related to an operated organ. In such an embodiment, the monitoring device may be used for postoperative monitoring of operated tissues and/or related tissues. Such monitoring may allow an early detection of post-operative complications of surgeries such as, abdominal, gynecologic, or thoracic surgeries, for example bleeding within an abdominal cavity and atelectasis.

It should be noted that such post-operative complications may be initiated unexpectedly, like in abdominal bleeding after a cesarean section (CS), a condition which requires medical intervention of a member of a treating medical staff. The monitoring of the operated tissue following specific procedures at specific locations may reduce or eliminate the requirement of a human supervision of the patient by a caretaker, such as an attendant nursing and/or medical staff and/or the use of ancillary imaging and/or laboratory tests.

In use, the monitoring device is used for monitoring dielectric related changes of the operated tissue and/or proximate or otherwise related tissues. For example, the monitoring device may be positioned such that it would monitor another tissue segment that is susceptible to bleeding in the abdomen, for example, the amount of blood within the chest may decrease as a consequence of abdominal bleeding and simple monitoring of the breathing signal would reveal such a decrease. For example, as depicted in FIG. 1, the monitoring device emits EM radiation toward the operated tissue and/or the related tissues and captures the reflections and/or passing EM waves therefrom in a plurality of sessions along a period of more than 3, 6, 12, 24, 48, 72 hours, intermediate periods and/or longer periods, as depicted in 101 and 102 and similarly to the described above. The reflections and/or passing EM waves which are captured in each session are analyzed for detecting dielectric related changes which are indicative to pathological patterns, as shown at 104. The dielectric related changes which are indicative to postoperative pathological patterns may be determined according to clinical experiments and/or a numerical simulation of postoperative pathological patterns in humans. Such a process allows detecting a dielectric related change that is indicative of fluid concentration change, such as fluid accumulation, optionally caused by bleeding. Optionally, the dielectric related changes are adjusted according to medical information that is related to the operated patient, for example the gender, the height, the weight, the body mass index (BMI), and/or the pathology of the patient.

Optionally, a registration process is performed in parallel to the performance of the EM radiation sessions, for example as described in International Patent Applications Numbers IL2008/001198 and IL2008/001199, filed on Sep. 4, 2008, which are incorporated herein by reference. In such an embodiment, the reflections and/or the EM waves may be calibrated according to the movement, the breathing cycle, and/or the posture of the patient.

The ability to notify the patient and/or the caretaker with regard to internal bleeding may allow diagnosing indications of hemodynamic shock, which may require complicated treatments that may save the patient life. An early notification may reduce the risks which are posed by these complicated treatments.

As the sessions may be repeated every few seconds, minutes, and/or hours, an early detection of the fluid accumulation is allowed. It should be noted that the detection is performed without a diagnostic imaging procedure, such as ultrasonographic examination or a computerized tomography scan, and without laboratory measurements of complete blood counts.

Optionally, the monitoring device is connected to a hemodynamic monitoring unit, such as sphygmomanometer and a pulse oxymeter. In such embodiments, the pathological patterns, which are detected by an analysis of the EM reflections and/or the EM waves, may be adjusted and/or calibrated according to outputs of the hemodynamic monitoring unit, such as blood pressure and pulse measurements, of the hemodynamic monitoring unit. For example, if the hemodynamic monitoring unit detects a reduction of blood pressure to less than 90/60 and/or an increase of pulse to more than 120 beats per minute. If the detected dielectric related change is indicative of bleeding, the notification indicates that there is a high chance for an internal bleeding.

In addition, many of the patients undergoing abdominal or thoracic surgery are patients inflicted with several diseases and comorbidities and require fluid resuscitation and close monitoring of the post operative period.

Such monitoring allows detecting atelectasis, which is a common pulmonary complication in patients which have been treated with thoracic and upper abdominal procedures. In case of atelectasis, airways are collapsed, thus, replaced by lung parenchyma and further with inflammatory agents, which result in change of regional dielectric coefficient. General anesthesia and surgical manipulation lead to atelectasis by causing diaphragmatic dysfunction and diminished chest wall motion due to pain. The atelectasis may be attributed to a reduced reflex response to aspiration. In such an embodiment, a bronchial pathway may be occluded and the distal airways may collapse sequentially. The atelectasis is typically basilar and segmental in distribution.

Monitoring internal bleeding after a surgical procedure allows verifying the reduction of the bleeding flow to a recovery level and notifying, as described above, if the recovery level is not decreased in a satisfactory rate. Additionally or alternatively, the monitoring allows generating an urgent alert in case of unexpected bleeding. Similarly, post-operative atelectasis may be developed and cause shortness of breath and multiple complications such as sepsis.

Optionally, as described above, the motoring device is as defined in International Patent Application Number IL2008/001198, filed on Sep. 4, 2008, which is incorporated herein by reference. In such an embodiment, the monitoring device is designed for monitoring the intrabody regions of hospitalized and unhospitalized patients, in various environments, for example, home, hospital, during rest or stressed activities. The monitoring device provides an estimation of the regional dielectric property.

As described above, the monitoring device may be used for monitoring post operation complications, such as an intense bleeding rate, an initiation of unexpected bleeding and atelectasis.

As described above, the monitoring device detects dielectric related changes. These changes may be indicative of changes which occur in internal body regions.

Optionally, the monitoring device is designed to scan sub regions in a sequential and/or non sequential depths and/or to focus on a specific location.

Optionally, the monitoring device is designed for detecting the complications by diagnosing the symptoms; the system provides early detection prior to consequent deterioration of clinical state, in a manner which enables proper treatment to avoid such deterioration.

Similarly to the described above, the monitoring device may have set up and sequential monitoring modes. When the device is in a set up mode, data pertaining to the operation that has been performed on or in relation to the intrabody region is provided by the user. In such a manner, a selected pattern may be monitored, such as an expected bleeding rate, as assessed by the physician at that time, e.g., 60-100 cc per hour. The received data may be used for defining a pattern of expected dielectric related changes and/or parameters and the analysis, which is based on the intercepted EM radiation, may be based on the defined pattern. For example, if in a certain surgery, a bleeding above 100 cubic centimeters (cc) is considered pathological, a respective alert may be defined. When a dielectric related change that is indicative to the accumulation of such an amount of blood or more is detected, the respective alert is presented to the patient and/or forwarded to the caretaker.

When the monitoring device is in a sequential monitoring mode, the aforementioned monitoring sessions are performed, as described above. Each monitoring session is used for characterizing the operated tissue current status is used for estimating a relative change.

The relative changes are analyzed according to the device configuration presets and according to manual configuration set by the medical staff and proper notifications are sent to the patient and/or directly to the medical staff thereof. Optionally, the notification may comprise suggestions of titration of the therapy that is provided to the patient and/or the treating caretaker and/or the directly to a therapy device.

Cerebral Edema

According to some embodiments of the present invention, the intrabody region is a traumatized cerebral tissue, such as a cerebral tissue of a patient suffering from a traumatic brain injury (TBI).

Patients involved in accidents, such as a motor vehicle accident (MVA), and in others situations may suffer from TBI in which the injury is inflicted on brain tissues. TBI may involve damage to the brain parenchyma and edema which evolves after a period of between a few hours and a few days after the injury. Such cerebral edema consists of intracellular pressure followed by vasogenic edema. Therefore, patients with TBI are usually put under a neurocritical care during which the cerebral edema is monitored. Such a neurocritical care allows delivering patient tailored targeted therapy to the patients. There is a critical importance to distinguish between bleeding that is drained and bleeding that accumulates and may result in a rise of the intracranial pressure, a life threatening condition. Therefore, patients are kept under supervision for at least 48 hours.

As described above, the monitoring device is configured for monitoring dielectric related changes in an intrabody region and/or region over a period of few hours and/or days. In the present embodiment, the monitoring device may be used for monitoring dielectric related changes which are indicative of the accumulation of blood in the brain. Placing the monitoring device in proximity to the injured side of the cranium and performing a plurality of EM radiation sessions, optionally continuously, allows monitoring dielectric related changes which are indicative of the development or nondevelopment of cerebral edema and generating notifications may alert the caretaker and/or the patient as to the accumulation of cerebral edema and optionally a recommendation to intervene for optimal treatment and/or before complications may occur. The dielectric related changes which are indicative of development or nondevelopment of cerebral edema may be determined according to clinical experiments and/or a numerical simulation of the development or nondevelopment of cerebral edema in humans. Optionally, the dielectric related changes are adjusted according to the medical information that is related to the monitored patient, for example the gender, the height, the weight, the body mass index (BMI), and/or the pathology of the patient.

Moreover, it may ease the supervision constraint. As described above, the monitoring device may be registered using an imaging modality. As elaborated above, a registration process may provide the entire information for allowing the detection of the expected physiological patterns Non Compliant Patient Monitoring Optionally, the monitoring device is designed to monitor or perform a measurement of low or non compliant patients, such as intensive care patients, new-born babies suffering from respiratory distress syndrome, patients under general anesthesia, for example during a surgery and children particularly of pre-school age.

The monitoring of dielectric related changes in pulmonary tissues allows early detection of respiratory problems in non compliant patients, such as the accumulation of air between the lungs and chest cavity walls, also known as pneumothorax, and/or partial blockage of the air passages by secretions. The early detection may prevent a deterioration of the medical condition of the patients and/or the development of complications. For example, the detection of one lung intubation (OLI) during anesthesia or intensive care may prevent a development of possible complications such as tissue hypoxia and irreversible brain damage.

As described above, the monitoring device may be a wearable device. Optionally, wearable device includes an attachment unit for attaching the wearable monitoring apparatus to the body of the user, and/or any other electronic component that may be worn out by the use of the wearable monitoring apparatus.

Similarly, it may be attached to the patient for a period, providing similar continuous monitoring of the patient For example as described in International Patent Applications Numbers IL2008/001198 and IL2008/001199, filed on Sep. 4, 2008 which are incorporated herein by reference. As such, the device may be used for monitoring patients outside of a hospital and/or any other medical service facility. In such an embodiment, the monitoring device may be used for monitoring patients, such as trauma patients, whom are to be transported to a medical center and may encounter respiratory difficulties. For example, a monitoring device may be placed on each side of the thorax of the patient, in proximity to the lungs, directly monitoring the dielectric related changes associated with breathing process of the chest cavity, and generating a notification when detecting an irregular dielectric related change. Optionally, the monitoring device is used for monitoring changes in the pulmonary fluid levels in patients, optionally in low or non compliant patients, which are transferred from one location to another, for example from an accident scene or a battle field to a hospital. For example, traumatic injuries such as pneumothorax, and/or the hemothorax, and/or to accumulation of airway secretions and/or blood may be detected and monitored along the transportation to the medical facility. Such monitoring allows notifying the caretaker when the patient's mechanical ventilation is subjected to mechanical hazards which may lead to changes in the pulmonary fluid levels or breathing patterns, such as a change of the fixation and suctioning secretions and positioning of a ventilation tube. It should be noted that when intubation is performed in suboptimal circumstances, for example when the caretaker is not experienced in performing the procedure, the chances that the ventilation tube may be misplaced are increased. Placing the ventilation tube too deep may cause lack of ventilation to one lung or due to damage the chest wall.

Optionally, the measurements by the monitoring device may be adjusted according to the ventilation parameters which are provided by the ventilation respiration machine. Optionally, the monitoring device issues warnings and/or changes parameters in the ventilation machine, for example, increases the pressure and/or the volume when some or all of the EM radiation sessions indicate poor expansion of the lung over a respiratory cycle.

In addition, the monitoring allows detecting breathing or ventilation problems which are indicative of patient distress, which may lead to irreversible danger to vital organs such as the brain and the heart.

It should be noted that by using a plurality of monitoring devices, a single caretaker may monitor a plurality of patients in a battlefield, an accident site or any other event in which more than one patient is found.

Acute Respiratory Distress Syndrome (ARDS)

Acute Respiratory distress syndrome (ARDS) is a severe lung disease caused by a variety of direct and indirect issues. It is characterized by inflammation of the lung parenchyma and increased permeability of pulmonary blood vessels leading to impaired gas exchange with concomitant systemic release of inflammatory mediators causing inflammation, hypoxemia and frequently resulting in multiple organ failure. This condition is often fatal, usually requiring mechanical ventilation in addition to treatment aimed at the inciting event and admission to an intensive care unit.

A less severe form is called acute lung injury (ALI). Today, ALI and ARDS patients are treated by intubation of the lungs, antibiotic and supportive care.

Optionally, the monitoring device is used for monitoring ALI and ARDS patients which are low or non compliant patients, or detection and monitoring of aspiration pneuomonia which may evolve into ALI condition.

Neonatal RDS

Respiratory distress syndrome of neonates is a condition in which the lungs have not reached maturity and therefore the neonates suffer from dyspnea and hypoxemia. The lack in surfactant causes the airways to be collapsed and impairs gas exchange. The condition is usually manifested by a specific pattern in Xray imaging called "groung glass" appearance. The condition is usually treated by intratubal administration of surfactant and supportive respiratory care.

In such an embodiment, the monitoring device may be placed on the newborn's chest or the premature baby's incubator for providing a notification to the caretaker that is indicative of a process that causes a dielectric related change within the lung parenchyma. Such a notification assists the caretaker in determining whether a further dose of surfactant is needed and/or when to withdraw a ventilation tube.

Stress Ergometry

Figure 7:
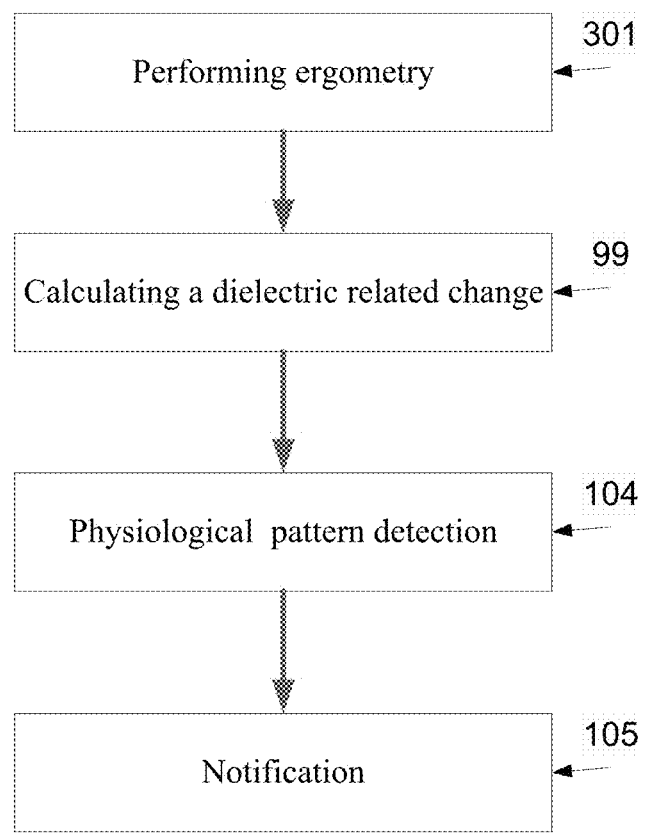
FIG. 7 is a flowchart of a method for monitoring an intrabody tissue of a patient performing a stress examination, according to some embodiments of the present invention.

Reference is now made to FIG. 7, which is a flowchart of a method for monitoring an intrabody region during a stress ergometry procedure and/or stress exercise, according to some embodiments of the present invention. As used herein a stress ergometry and/or a stress exercise are diagnosis procedures based on either electrocardiography and/or echocardiography. It should be noted that the stress ergometry and/or a stress exercise may include any diagnosis procedure which is based on electrocardiography, echocardiography, and/or any examination of a bodily activity and/or functioning of the patient and/or an organ thereof.

Blocks 99, 104, and 105 are as described above in relation to FIG. 7. However, as shown at 301, FIG. 7 depicts a method in which the dielectric related changes are monitored during a stress exercise. In such an embodiment, the monitored intrabody region is active while the patient performs a stress examination. In such an embodiment, fluid that is accumulated in the lungs during a stress examination may be monitored and a notification that is indicative of the accumulation rate and/or amount is outputted. Optionally, the monitoring is performed as described in International Patent Applications Numbers IL2008/001198 and IL2008/001199, filed on Sep. 4, 2008, which are incorporated herein by reference.

Exercise electrocardiography is a common, non-invasive test for diagnosing various pathologies, such as myocardial ischemia. Extensive data shows that the test has a sensitivity level of 68% and a specificity of 77%, see Noninvasive tests in patients with stable coronary artery disease. N Engl J Med, 344:1840, Jun. 14, 2001, clinical practice, which is incorporated herein by reference. Other non-invasive tests, such as radionuclide imaging and stress echocardiography have better sensitivity and specificity. The monitoring of the dielectric related changes during the stress examination allows detecting high-risk patients in which the measured lung water content increases and in which a more aggressive treatment is advisable. It may improve the sensitivity and specificity of each of the described exercise tests.

Optionally, the monitoring device is used for diagnosing coronary abnormalities based on dielectric related changes of pulmonary tissues which are detected during a stress examination.

Optionally, before the monitoring is initiated, the monitoring device is calibrated. During the calibration stage, an EM radiation session or sessions for assessing the level of fluids within the pulmonary tissues is performed. Such a measurement may be used for detecting changes which may occur during the stress examination, after the stress examination is initiated.

Exemplary Monitoring Device

Figure 8:
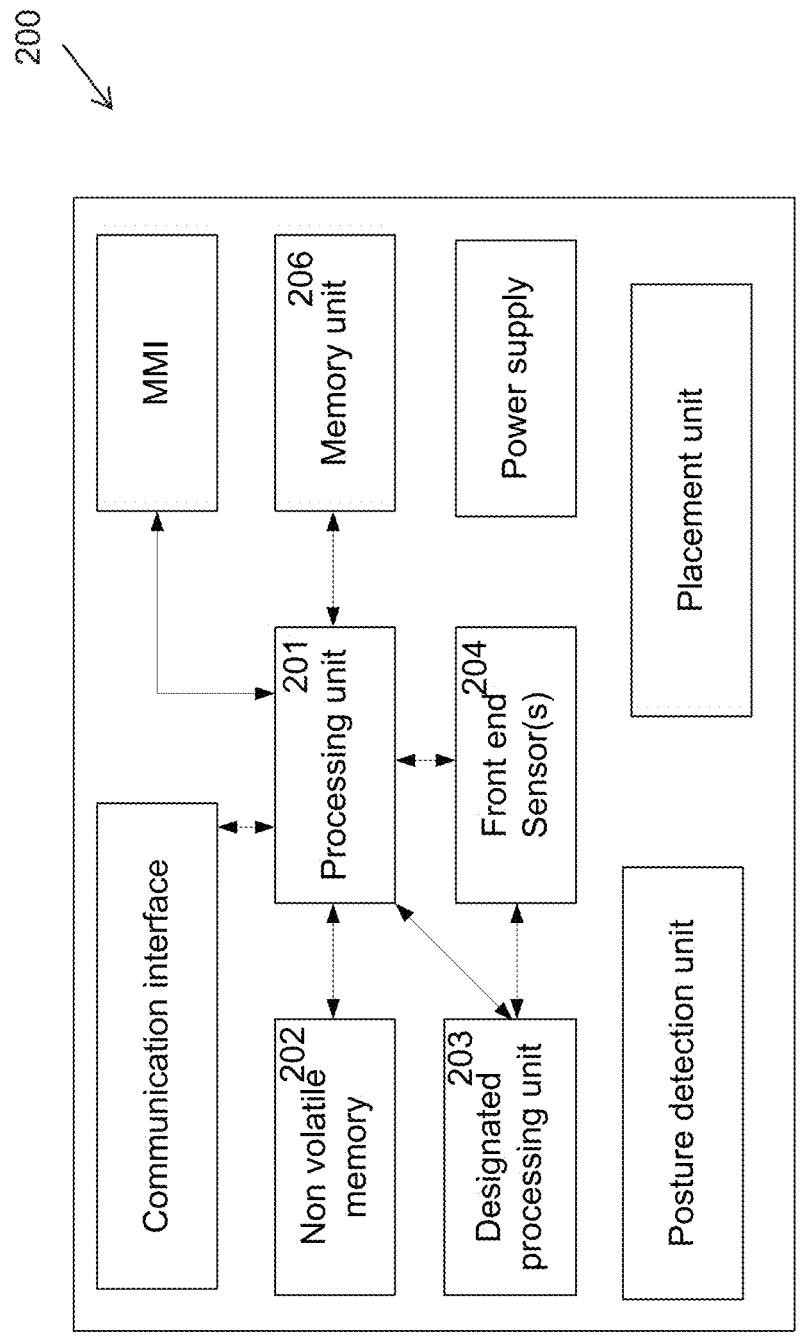
FIG. 8 is a schematic illustration of a monitoring device for monitoring dielectric related changes in an intrabody tissue, according to some embodiments of the present invention.

Reference is now also made to FIG. 8, which is a schematic illustration of a set of components 200 of an exemplary monitoring device, according to some embodiments of the present invention. Optionally, the exemplary monitoring device is designed as a wearable and/or as a stationary monitoring device, for example as described in International Patent Applications Numbers IL2008/001198 and IL2008/001199, filed on Sep. 4, 2008, which are incorporated herein by reference. The monitoring device may be used for implementing any of the aforementioned method.

The exemplary device which is depicted in FIG. 8 comprises a central processing unit (CPU) and/or a digital signal processing (DSP) which may be referred to herein as a processing unit 201. Optionally, the processing unit 201 runs a real-time operating system (RTOS) that is responsible for coordinating all functions of the monitoring device 100. The processing unit 201 is optionally used for analyzing the outputs of the one or more front-end sensors 204 which are described below. Optionally, the one or more front-end sensors 204 capture signals which are forwarded to the processing unit 201 that calculates medical indices of interest, which is optionally based on physiological, anatomical and/or clinical parameters. The medical indices of interest are based on a dielectric related change that is reflected from the signals. The medical indices of interest may be used for detecting a pathological pattern. For example, the processing unit 201 may compare between the calculated parameters and a set of one or more predefined values and sets flags accordingly, for example as described below. The data which is calculated by the processing unit 201 is optionally used for generating one or more alerts and/or notifications, as further described above. It should be noted, that the term processing unit means a local processing unit, a distributed processing unit, and/or a remote processing unit which is used for performing the functioning of the processing unit which is described herein. In an embodiment in which the processing unit is remote, the data which is forwarded to the processing unit is transmitted for remote processing by the remote processing unit.

The monitoring device 100 further comprises a memory unit 202, such as a non volatile memory, that is designed for storing the operating system and parameters which are needed for the functioning of the monitoring device 100. Optionally, the memory unit 202 is used for recording readings of reflections from the intrabody regions and/or calculations which are based thereupon, for example as further described above. Optionally, as outlined above, the dielectric related properties of the monitored intrabody region, such as the fluid contents, for example tissue fluid contents which are calculated according to EM waves from the tissue, are recorded in the memory unit 202. Such a recording allows examining changes in the predefined and/or known biological patterns, such as in the pathological pulmonary fluid content, along a period that lasts between few hours and days, for example as outlined above. The recording allows calculating one or more baselines and/or the identification of a normal range which are adjusted according to the specific user. Optionally, the memory unit 202 is used for recording readings of medical sensors which are connected to the monitoring device 100 and/or embedded therein. Optionally, the memory unit 202 is used for storing additional information, such as application executables codes, configuration files for the processing unit 201, preset parameters, long term state parameters and tables. The memory unit 202 may be used for storing additional user related data, such as the user identification information, version information, user specific thresholds, authentication and/or security keys.

The monitoring device 100 further comprises a rapid access volatile memory unit 206, such as a dynamic random access memory (DRAM), a synchronous DRAM (SDRAM), and/or any other volatile memory for storing data that is needed to be accessed in a limited time for short terms. It may be interfaced by the processing unit 201, the below mentioned designated IC and/or any other component of the monitoring device 100.

Optionally, the monitoring device 100 comprises a designated processing unit 203, such as a designated integrated circuit (IC), for example an application-specific integrated circuit (ASIC) or a field-programmable gate array (FPGA) that contains logic blocks and programmable interconnects which are programmed to implement some of the functions required to process the data from the sensors front-ends. The designated processing unit 203 communicates with the processing unit 201, the memory unit 202, and/or with other components of the device for various tasks. Additionally or alternatively, the designated processing unit 203 may also implement any of the other blocks as an integrative solution. For example, the FPGA or ASIC may incorporate the processing unit 201 and/or another processing unit. Optionally, the logic blocks are programmed to implement monitoring methods as described above.

As described above and depicted in FIG. 8, the monitoring device 100 further comprises one or more probes, such as front-end sensors 204, for example EM transceivers, for transmitting a plurality of electromagnetic (EM) waves toward the thorax of the user and for capturing reflections thereof from an area of interest or any EM waves passing therethrough, such as the pulmonary tissues of the user. In some embodiment, the beam is transmitted in a desired pulse and allows the capturing of a reflection thereof from various areas on the surface of the user's body. Optionally, the capturing is adjusted according a selected operational mode, for example according to a selected swept frequency, a selected frequency hopping chirp, and the like. Other modes and/or gating patterns according to which the beam is transmitted and allows the capturing thereof are described in International Patent Applications Numbers IL2008/001198 and IL2008/001199, filed on Sep. 4, 2008, which are incorporated herein by reference.

In such a mode, time gating may be used for focusing on a specific reflection, for example as described in International Patent Applications Numbers IL2008/001198 and IL2008/001199, filed on Sep. 4, 2008, which are incorporated herein by reference. The shape of the pulse may be generated using different shaping techniques.

In some embodiments of the present invention, the front-end sensors 204 include EM transducers which are designed for transmitting one or more pulses of EM radiation and intercepting the EM radiation from monitored tissues and/or organs of the monitored patient. Optionally, the monitored tissues are internal tissues, such as the pulmonary tissue. The intercepted EM radiation is converted to a signal having different features that allows evaluating dielectric related properties of the monitored tissues and/or organs, for example as described below. The EM transducers are optionally designed to continuously transmitting and analyzing the intercepted EM radiation for monitoring dielectric related properties of the monitored tissues and/or organs, which may be referred to herein, for brevity, as the monitored tissues.

Optionally, in order to achieve high range resolution while keeping the implementation relatively simple close range detection pulses are used. The shorter the pulse the higher is the space resolution. Such pulses are known in the art and therefore not discussed in great detail.

Optionally, the EM transducer is designed to transmit one or more stable frequency continuous wave (CW) radio signals and then to receive the intercepted EM radiation from internal tissues and/or objects. The one or more CW radio signals may be transmitted, simultaneously or sequentially. For example, the CW radio signals may be transmitted in frequencies such as 900 MHz and 2.5 GHz. The CW radio signals may sweep one or more frequency ranges allowing measuring intercepted EM radiation in wide range of frequencies. CW signals as well as any narrow band signal may achieve high dynamic range by using narrow filtering around the used frequencies. The narrow filter may track the signal over time, for example, it may sweep together with the signal.

Optionally, the spatial and/or timing information is extracted by using multiple frequencies. Such information is mainly conveyed in the received phase of the signal. Optionally where a low number of frequencies which are not well spread over a large bandwidth results in a relatively poor or void time resolution. A single frequency allows generating differential measurements for measuring a movement and/or a displacement of a tissue and/or an organ by sensing a change over time of mainly the phase but also the amplitude of the intercepted EM radiation. When a dielectric coefficient of a tissue and/or an organ changes, mainly the amplitude but also the phase of the intercepted EM radiation may respectively change. Multiple CW signals with spatial resolution thereof are indicative to a localized movement and/or displacement and/or dielectric related changes.

As described above, the CW radio signals may be transmitted in one or more continuous or intermittent EM radiation sessions. In such an embodiment, known changes in internal organs may be used for performing differential measurements that may be indicative of dielectric related properties of a monitored tissue and/or organ. Examples for physiological processes during which the changes in the internal organs are known may be heart beat cycle and/or a breathing cycle.

For example, the breathing cycle changes the dielectric coefficient of the pulmonary tissue. Such a change affects mainly the amplitude but also the phase of a CW signal which is reflected from the pulmonary tissue. A record that documents changes in the dielectric coefficient of the pulmonary tissue during at least one breathing cycle may be used as a reference for monitored tissues and/or organs, for example monitoring the fluid content in a monitored pulmonary tissue, for example as described in International Patent Applications Numbers IL2008/001198 and IL2008/001199, filed on Sep. 4, 2008, which are incorporated herein by reference.

In another exemplary embodiment, the dielectric coefficient of a pulmonary tissue may be monitored by tracking a differential measurement calculated based on the intercepted EM radiation from the interface between the lung and the heart during the systolic and diastolic phases of the cardiac cycle. As the movements of the heart are relatively rapid ~1 hertz (Hz) with respect to posture changes and movement, such a calculation reduce the effects of posture change and movement.

Reflections from the heart through the lung are changed, in phase and/or amplitude, during a systole diastole cardiac cycle. In some embodiments of the present invention, these reflections are used to evaluate a fluid content in a monitored pulmonary tissue. Thus, in order to improve the accuracy of this evaluation, the effect of the systole diastole cardiac cycle on the reflection has to be taken into account.

Changes in the phase and amplitude of EM radiation intercepted from the heart through the lung are indicative of dielectric related properties changes where the measurement itself is posture resilient. In particular, the phase of the systole-diastole differential measurement is indicative of a dielectric related change in the lung. Changes in the concentration of fluids in the lung affect the phase velocity (EM radiation propagation speed) and therefore may be used for evaluating the fluid content in the lung. The amplitude of the differential signal is also indicative to dielectric related change in the lung, as a pulmonary tissue with a certain concentration of fluids absorbs more of EM radiation that propagates therethrough than a pulmonary tissue with a lower concentration. The higher is the absorptions of reflections the lower are the reflections from the heart. Optionally, the reduced effect of the posture on the reflections is identified and further reduced using the posture detection methods which are described below.

In some embodiments of the present invention, the one or more EM transducers use a simplified narrow band and/or a multiple-band antenna, with one continuous band or several bands, which are matched to the monitored tissue and/or organ. Optionally, a placement mechanism or unit, such as the placement unit which is described below, is used for shifting the matching bands of the antenna according to the positioning thereof. Optionally, the CW signals are shifted each separately or jointly, so as to achieve optimal sensitivity to one or more parameter, such as shifts in respiration and heart rates.

Optionally, the CW signals referred to in this patent are equivalent to narrow-band signals, and all descriptions referred to such CW signals may be equivalently referred to the narrow-band signals. As used herein a narrow-band signal means a signal spreading over a small frequency band, for example up to 50 MHz, optionally modulated and used to expand the band of the transmitted energy. Such modulation may be frequency hopping, chirp, frequency-shift keying (FSK), phase-shift keying (PSK), amplitude Shift Keying (ASK) and the like. In such an embodiment, the EM transducers may de-modulate the reflections to compress the band back before further filtering and detection for improved sensitivity and dynamic range.

Optionally, the frequencies of the narrow band signals are 900 Mega Hertz (MHz) and/or 2.4 gigahertz (GHz) industrial, scientific, and medical (ISM) bands. Optionally, two frequencies, such as the aforementioned two frequencies, may be combined to improve time resolution and/or to separate reflections from neighboring interfaces, or may be used for improved sensitivity. In such an embodiment, the lower frequency penetrates deeper and less sensitive to small displacements. In such an embodiment, radiation in different frequency may be produced sequentially or simultaneously.

Optionally, narrow-band signals may be used jointly with pulsed wideband signals so as improve the overall sensitivity and robustness of the transmission session. As commonly known, a narrow band antenna is directive and allow more power to be used for the narrow band signals. Optionally, the pulse wideband transmission may achieve improved spatial resolution while the narrow band signals may improve the penetration depth and extract information from deeper layers.

Optionally, the one or more front-end sensors 204 includes additional medical sensors, such as an electrocardiogram (ECG), an electromyogram (EMG), ultrasound transducers, pulse oximeters, blood pressure sensors, accelerometers, tilt-meters, coagulometers, and optical blood saturation detectors.

In one example of the present invention, the wearable monitoring device is attached to the skull of a user and used for monitoring a build up of intra-cranial edema fluid which may be a consequence of a head injury. The device may be focused on a specific location according to inputs from an imaging modality such as an MRI and/or a CT modality, either automatically and/or through a manual user interface. Alternatively, a broad region should be monitored either by a wide range of irradiated region from a single device or by a multiple transducers in a configuration as described below. The monitoring period is relatively short of few days, and the measurements frequency is relatively high specifically right after initial placement of every few minutes.

Optionally, the one or more front-end sensors 204 include one or more EM transceivers which are designed for generating sharp pulses. Optionally, the EM transceivers are connected to and/or include one or more amplifiers, such as a low noise amplifier (LNA). Optionally, the EM transceiver having a slim profile that allows the manufacturing of a slim monitoring device 100, for example as described in International Patent Applications Numbers IL2008/001198 and IL2008/001199, filed on Sep. 4, 2008 which are incorporated herein by reference.

Optionally, the EM transceiver is designed for sampling pulse signals which are echoed from an internal area in the body of the user, such as the pulmonary tissues, and indicative of the dielectric related properties of fluids, such as water, blood, and/or inflammation fluids therein.

Optionally, each EM transceiver utilizes one or more antennas for transmitting and/or intercepting EM signals. Each antenna may be configurable by setting antenna controls.

In some embodiments of the present invention, the antenna is a low reverberation antenna, such as a planar wide band antenna adapted for reducing the effect of reverberations upon the quality of signal transmission. Such an antenna produces a short duration fast-decaying pulses for improved time and range resolution. Optionally, the antenna terminates the radiation using lumped resistors to reduce reverberations, which may be referred to as re-ringing of currents, from the far end of the antenna and emulate an infinite antenna, without a need for printing tapered resistive layers.

A Reference Intrabody Region

According to some embodiments of the present invention, the monitoring device is designed to monitor a reference intrabody region for allowing the detection of a reference dielectric related change. The reference dielectric related change is used in combination with the dielectric related change for detecting a physiological pattern, for example as described above. For example, the reference dielectric related change may be used for scaling, calibrating, and/or adjusting the dielectric related change. The detected dielectric related changes may be used for notifying the patient and/or the caretaker about various physiological patterns in the intrabody region, for example as described above. Optionally, the reference intrabody region and the intrabody region are selected from the same organ. In such a manner, a physiological pattern may be identified when a difference between the dielectric related change and reference dielectric related change is formed, for example when blood is accumulated in the intrabody region and not in the reference intrabody region. Optionally, the reference intrabody region and the intrabody region are selected from similar organs such as the left and the right lung. In such an embodiment, a physiological pattern may be identified when a difference between the dielectric related change and reference dielectric related change is formed when fluid is accumulated in one of the lungs. Optionally, the monitoring device comprises two or more probes for separately monitoring the two regions. Optionally, the probes share the processing units 201-203. Optionally, each probe is a separate unit having separate processing units. Each probe monitors the changes of dielectric related properties in one region for example a lung, for example similarly to the described in International Patent Applications Numbers IL2008/001198 and IL2008/001199, filed on Sep. 4, 2008 which are incorporated herein by reference and to the described above. In another embodiment, a single sensor switches between a number of different reception states, such as different reception angles, or depths, for intercepting reflections from another region. The sensor may include two or more radiating elements for allowing beam stearing as described in International Patent Applications Numbers IL2008/001198 and IL2008/001199, filed on Sep. 4, 2008 which are incorporated herein by reference. The dual monitoring allows matching between two different readings and/or the two different analysis outputs. Comparing readings may allow a detection of physiological processes as the mismatch between the measured dielectric related properties is associated with an estimated change in the regional dielectric related properties.

The measurement of the ventilation by multiple probes positioned with respect to each lung or lobe, may indicate the efficacy of the ventilation of a respective lung, and providing sequential measurements may provide indication regarding exacerbation or amelioration processes in any of the lungs. Differences between the measurements of the two probes may indicate a difference in the efficacy of the ventilation of the lungs. The probes may be wearable and/or designed to be positioned in distance from the patient in static position. The static positioning is mostly suitable for neonates who are considerably static for long periods.

Figure 9:
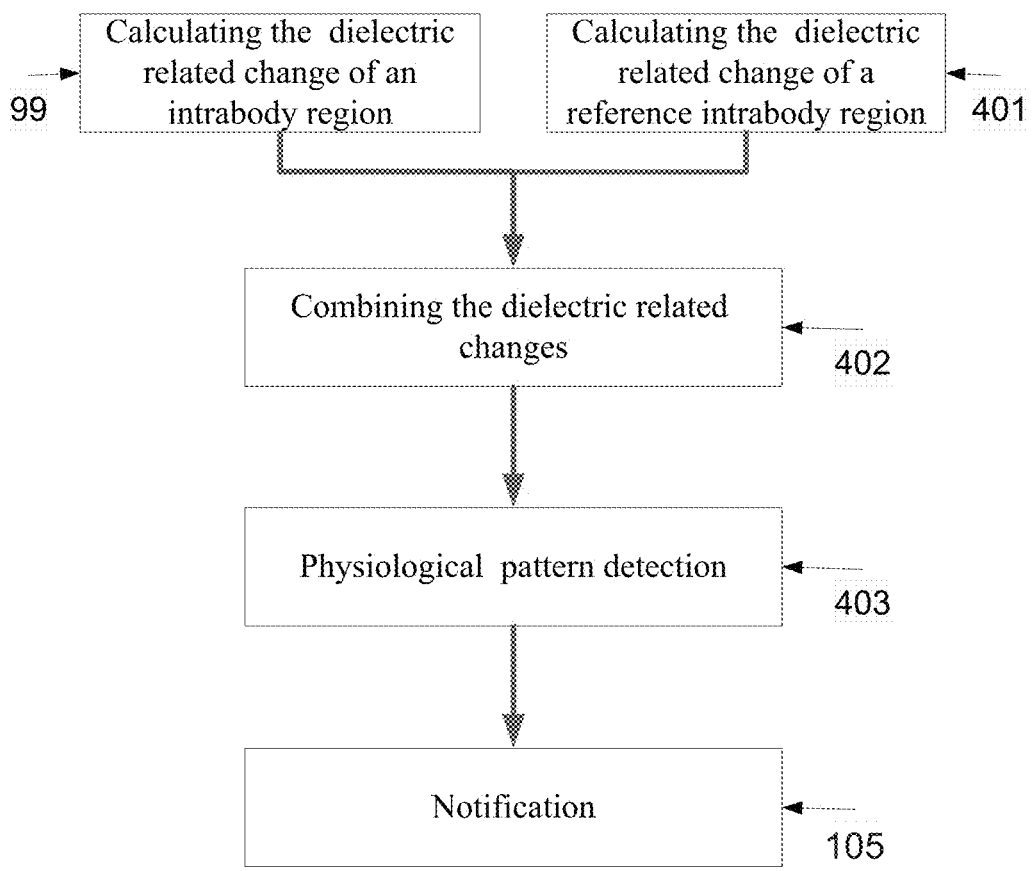
FIG. 9 is a flowchart of a method for detecting a pathological pattern of a pulmonary tissue by calculating a difference between the dielectric coefficients of tissues from the left lung and the right lung, according to some embodiments of the present invention.

For example, FIG. 9 depicts a method for detecting a pathological pattern of a pulmonary tissue by combining dielectric related changes in the reference intrabody region and the intrabody region, for example in the left lung and in the right lung, according to some embodiments of the present invention. Blocks 99 and 104 are as described in relation to FIG. 1. However FIG. 9 further describes the calculation of a reference dielectric related change in a reference region, as shown 401 and the combination of the reference dielectric related change with the dielectric related change, as shown at 402, for evaluating a pathological pattern, as shown at 404.

Optionally, reflections of EM radiations are intercepted from the reference intrabody region and the intrabody region, for example using the aforementioned probes, simultaneously, alternately, and/or sequentially. The intercepted reflections allow calculating the dielectric related changes, each for example as described above. Then, as shown at 402, the dielectric related changes are combined. The combination allows, as shown at 403, identifying, for example by a match with a set of records, a substation, and/or scaling, the identification of a pathological pattern in the intrabody region and/or in the reference intrabody region. Now, as shown at 104, a notification indicating the pathological pattern is outputted, optionally in a similar manner to the described above.

It is expected that during the life of a patent maturing from this application many relevant systems and methods will be developed and the scope of the term a radiation, a monitoring device, and an EM radiation session is intended to include all such new technologies a priori.

As used herein the term "about" refers to ±10.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

What is claimed is:

1. A wearable monitoring device for monitoring an intrabody region during a stress ergometry test for detecting a pathological state in a patient, comprising:
   at least one probe comprising at least one transducer configured for transmitting to and intercepting electromagnetic (EM) radiation from at least one intrabody region of the lungs of the patient while said patient is performing the stress examination test;
   at least one hardware processor in communication with the at least one probe, and in communication with the at least one of a communication interface and a display;
   a non-transitory memory having stored thereon a code for execution by the at least one hardware processor of the wearable monitoring device, comprising:
      code for detecting a breathing cycle of the patient according to an analysis of the intercepted EM radiation transmitted by the at least one probe;
      code for calculating a dielectric related change of the at least one intrabody region by analyzing respective said intercepted EM radiation transmitted by the at least one probe in view of a differential signal computed according to the detected breathing cycle; and
      code for detecting a change in measured fluid in the lungs during said stress examination test according to said dielectric related change,
      wherein said change in measured fluid is detected relative to a baseline level of fluid within the at least one intrabody tissue, wherein the baseline level of fluid is measured during a calibration stage performed before monitoring of the stress examination test is initiated; and
      code for outputting via at least one of the communication interface and the display, a notification indicative of said change in measured fluid in the lungs during said stress examination test, wherein said change in measured fluid in the lungs is indicative of the pathological state of the patient with higher sensitivity and/or specificity in comparison to stress examination test alone.

2. The wearable monitoring device of claim 1, wherein said detecting a change in measured fluid in the lungs includes:
   code for estimating an expected signal of intercepted electromagnetic radiation, and
   code for matching said estimated signal to a detected signal of intercepted electromagnetic radiation, thereby detecting said change in measured fluid in the lungs.

3. The wearable monitoring device of claim 1,
   wherein said non-transitory memory further has stored thereon code for computing a medical index of interest by comparing the dielectric related change of the at least one intrabody region to estimated values of dielectric related change during the stress examination test.

4. The wearable monitoring device of claim 1, wherein the at least one transducer of said at least one probe, said non-transitory memory and said at least one hardware processor are contained in a housing designed for being disposed on the body of the patient performing the stress examination test.

5. The wearable monitoring device of claim 1, wherein said at least one probe is arranged to intercept EM radiation which passes through the intrabody region.

6. The wearable monitoring device of claim 1, wherein said dielectric related change is analyzed to detect an indication of a computed expected change in a plurality of properties of said intrabody region.

7. The wearable monitoring device of claim 6, wherein said plurality of properties of said intrabody region indicated by the calculated dielectric related change comprises a member of a group consisting of a density, a size, a shape, and a concentration of fluids.

8. The wearable monitoring device of claim 1, further comprising code for diagnosing at least one coronary abnormality based on the detected change in measured fluid in the lungs during the stress examination test.

9. The wearable monitoring device of claim 1, wherein the differential signal is analyzed in relation to expected changes in the dielectric coefficient of the at least one intrabody region during the detected breathing cycle.

10. The wearable monitoring device of claim 9, wherein the expected changes in the dielectric coefficient are obtained from a reference chest wall model adjusted according to the detected breathing cycle.

11. The wearable monitoring device of claim 1, wherein the dielectric related change of the at least one intrabody region is calculated at least according to changes of amplitude of the differential signal.

12. The wearable monitoring device of claim 1, wherein the differential signal is computed as the differences between intercepted EM radiation received during inhalation and intercepted EM radiation received during exhalation of the detected breathing cycle.

13. A method for monitoring an intrabody region during a stress ergometry test for detecting a pathological state in a patient, comprising:

intercepting electromagnetic (EM) radiation transmitted by at least one probe from the at least one intrabody region of the patient performing the stress examination test in at least one EM radiation session;

detecting a breathing cycle of the patient according to an analysis of the intercepted EM radiation transmitted by the at least one probe;

calculating a dielectric related change of the at least one intrabody region by analyzing respective said intercepted EM radiation transmitted by the at least one probe in view of a differential signal computed according to the detected breathing cycle;

detecting a change in measured fluid in the lungs during said stress examination test according to said dielectric related change, wherein said change in measured fluid is detected relative to a baseline level of fluid within the at least one intrabody tissue, wherein the baseline level of fluid is measured during a calibration stage performed before monitoring of the stress examination test is initiated; and outputting a notification indicating said change in measured fluid in the lungs during said stress examination test, wherein said change in measured fluid in the lungs is indicative of the pathological state of the patient with higher sensitivity and/or specificity in comparison to said stress examination test alone.

14. The method of claim 13, further comprising diagnosing at least one coronary abnormality based on the detected change in measured fluid in the lungs during the stress examination test.

* * * * *